United States Patent
Heindl et al.

(10) Patent No.: US 8,569,515 B2
(45) Date of Patent: Oct. 29, 2013

(54) DIRECTED SYNTHESIS OF OLIGOPHOSPHORAMIDATE STEREOISOMERS

(75) Inventors: Dieter Heindl, Paehl (DE); Dirk Kessler, Peiting (DE); Angelika Roesler, Sindelsdorf (DE); Christoph Seidel, Weilheim (DE); Wilma Thuer, Kulmbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/099,630

(22) Filed: May 3, 2011

(65) Prior Publication Data

US 2011/0212861 A1    Sep. 1, 2011

Related U.S. Application Data

(63) Continuation of application No. PCT/EP2009/008370, filed on Nov. 25, 2009.

(30) Foreign Application Priority Data

Nov. 27, 2008 (EP) .................................... 08020625
Dec. 23, 2008 (EP) .................................... 08022319

(51) Int. Cl.
*C07F 9/24* (2006.01)
(52) U.S. Cl.
USPC ...................................................... 549/220
(58) Field of Classification Search
USPC .............................. 506/15; 549/220; 436/501
See application file for complete search history.

(56) References Cited

FOREIGN PATENT DOCUMENTS

| EP | 1431297 A1 | 6/2004 |
|---|---|---|
| EP | 1431298 B1 | 3/2006 |
| EP | 1186613 B1 | 11/2006 |
| WO | 92/00091 A1 | 1/1992 |
| WO | 92/00252 A1 | 1/1992 |
| WO | 95/23160 A1 | 8/1995 |
| WO | 03/104249 A1 | 12/2003 |

OTHER PUBLICATIONS

International Search Report issued Feb. 2, 2010 in PCT Application No. PCT/EP2009/008370.
Alul, Rushdi H. et al., "Oxalyl-CPG: a labile support for synthesis of sensitive oligonucleotide derivatives," Nucleic Acids Research, 1991, pp. 1527-1532, vol. 19, No. 7.
Baschang, Von Gerhard and Kvita, Vratislav, "Imidophosphate als neue Nucleotid-Derivate," Angewandte Chemie, 1973, pp. 43-44, vol. 85, No. 1 (chemical structures only).
Behrens, Carsten and Dahl, Otto, "Synthesis of Achiral Linker Reagents for Direct Labelling of Oligonucleotides on Solid Supports," Nucleosides & Nucleotides, 1999, pp. 291-305, vol. 18, No. 2.

Béres, J. et al., "Stereospecific Synthesis and Antiviral Properties of Different Enantiomerically Pure Carbocyclic 2'-Deoxyribonucleoside Analogues Derived from Common Chiral Pools: (+)-(1R,5S)- and (−)-(1S,5R)-2-Oxabicyclo[3.3.0]oct-6-en-3-one," Journal of Medicinal Chemistry, 1990, pp. 1353-1360, vol. 33.
Fathi, Reza et al., "Synthesis and Properties of Combinatorial Libraries of Phosphoramidates," Journal of Organic Chemistry, 1996, pp. 5600-5609, vol. 61.
Froehler, Brian C., "Deoxynucleoside H-Phosphonate Diester Intermediates in the Synthesis of Internucleotide Phosphate Analogues," Tetrahedron Letters, 1986, pp. 5575-5578, vol. 27, No. 46.
Ghosh, P. K. et al., "Advances in Functionalization of Polymer supports for Synthesis and Modification of Oligonucleotides," Journal of the Indian Chemical Society, Apr. 1998, pp. 206-218, vol. 75.
Grasby, Jane A. and Williams, David. M., "Nucleotides and Nucleic Acids," Organophosphorus Chemistry, 1999, pp. 161-230, vol. 29.
Hansch, Corwin et al., "A Survey of Hammett Substituent Constants and Resonance and Field Parameters," Chemical Reviews, 1991, pp. 165-195, vol. 91.
Hyodo, Mamoru et al., "Utility of Azolium Triflates as Promoters for the Condensation of a Nucleoside Phosphoramidite and a Nucleoside in the Agrawal's Stereoselective Synthesis of Nucleoside Phosphorothioates," European Journal of Organic Chemistry, Dec. 2005, pp. 5216-5223, vol. 24.
Iyer, Radhakrishnan P. et al., "Solid-Phase Stereoselective Synthesis of Oligonucleoside Phosphorothioates: The Nucleoside Bicyclic Oxazaphospholidines as Novel Synthons," Tetrahedron Letters, 1998, pp. 2491-2494, vol. 39.

(Continued)

*Primary Examiner* — Kristin Vajda
(74) *Attorney, Agent, or Firm* — Faegre Baker Daniels LLP

(57) ABSTRACT

The trivalent phosphorous atom of a compound is reacted with a reagent in such a manner that a stable phosphate mimetic or a specifier is formed. Phosphoramidites with a phosphorous atom containing at least one hydroxyl residue which is provided with a protective group are reacted for this purpose with a free hydroxyl group: In the first synthesis cycle the hydroxyl group is linked to a solid support via a cleavable or non-cleavable linker. In further synthesis cycles the hydroxyl group is created by cleavage of the protective group from the growing oligomer. This results in formation of a phosphorous acid triester which is reacted with azides. By selecting suitable monomers for the synthesis which have a defined stereoconformation compounds of Formula 1 are produced in a stereocontrolled manner.

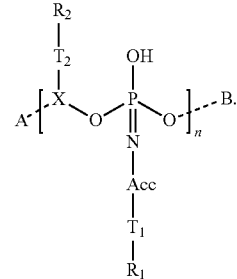

(Formula 1)

10 Claims, 6 Drawing Sheets

(56) References Cited

OTHER PUBLICATIONS

Kawakami, Junji et al., "Introduction of Peptide Functions into DNA by Nucleic Acid Peptides, NAPs," Chemistry Letters, 2004, pp. 1554-1555, vol. 33, No. 12.

Korshun, Vladimir A. et al., "Reagents for Multiple Non-Radioactive Labelling of Oligonucleotides," Synthetic Communications, 1996, pp. 2531-2547, vol. 26, No. 13.

Lam, Kit S. et al., "A new type of synthetic peptide library for identifying ligand-binding activity," Nature, Nov. 7, 1991, pp. 82-84, vol. 354.

Nielsen, John and Caruthers, Marvin H., "Directed Arbuzov-Type Reactions of 2-Cyano-1,1-dimethylethyl Deoxynucleoside Phosphites," Journal of the American Chemical Society, 1988, pp. 6275-6276, vol. 110.

Oka, Natsuhisa et al., "Stereocontrolled synthesis of oligonucleoside phosphorothioates and PO/PS-chimeric oligonucleotides by using oxazaphospholidine derivatives," Nucleic Acids Symposium, 2008, pp. 335-336, Series No. 52.

Ranasinghe, Rohan T. and Brown, Tom, "Fluorescence based strategies for genetic analysis," Chemical Communications, 2005, pp. 5487-5502, vol. 44.

Tomasz, J. and Ludwig, J., "Instability of the Phosphodiester-Amide Interribonucleotide Bond in Neutral Aqueous Solution," Nucleosides & Nucleotides, 1984, pp. 45-60, vol. 3, No. 1.

Tsarev, Vasily N. et al., "Novel Highly Efficient P-Chiral Ferrocenylimino Diamidophosphite Ligands for Pd-Catalysed Asymmetric Allylation," European Journal of Organic Chemistry, May 2005, pp. 2097-2105, vol. 10.

Valis, Linda and Wagenknecht, Hans-Achim, "Phenanthridinium as an Artificial DNA Base: Comparison of Two Alternative Acyclic 2'-Deoxyribose Substitutes," Synlett, 2007, pp. 2111-2115, vol. 13.

Vorob'ev, O. E. et al., Doklady Akademii Nauk SSSR, 1966, pp. 95-98, vol. 166, No. 1 (chemical structures only).

Wilk, Andrzej et al., "Deoxyribonucleoside Cyclic N-Acylphosphoramidites as a New Class of Monomers for the Stereocontrolled Synthesis of Oligothymidylyl- and Oligodeoxycytidylyl- Phosphorothioates," Journal of the American Chemical Society, 2000, pp. 2149-2156, vol. 122.

Formula 1

Formula 2

Formula 3

Formula 4

DIRECTED SYNTHESIS OF OLIGOPHOSPHORAMIDATE STEREOISOMERS

RELATED APPLICATIONS

This application is a continuation of PCT/EP2009/008370 filed Nov. 25, 2009 and claims priority to EP 08022319.1 filed Dec. 23, 2008 and to EP 08020625.3 filed Nov. 27, 2008.

FIELD OF THE INVENTION

The present invention is directed to oligomeric compounds consisting of monomeric units having a spacer segment covalently bound to a phosphoramidate moiety. Substituents are attached independently at both the spacer segment, and at the phosphoramidate moiety in such manner that the stereochemistry is defined. The oligomers consist of either a random or a predefined sequence of units. A plurality of individual sequences can be created by varying the substituents of the incorporated monomers. The substituents differ from each another due to the choice of the preparator and the purpose of the prepared oligomers. The individual substituents can be selected from a broad range of chemical functionalities.

BACKGROUND OF THE INVENTION

The phosphoramidate modification of oligonucleotides is long known (Vorob'ev, O. E., et al., Doklady Akademii Nauk SSSR 166(1) (1966) 95-98). The frequent used synthesis is based on the strategy of converting an H-Phosphonate with CCl4 in the presence of an nucleophilic amine to the corresponding phosphoramidate (Froehler, B. C., Tetrahedron Letters 27(46) (1986) 5575-5578).

This strategy is also used for building up non-nucleosidic oligophosphoramidates with amine residues at the P atom (WO 95/23160=EP 0 751 948) and Fathi, R., et al., J. Org. Chem. 61 (1996) 5600-5609) which are modified in different manners. The residues are introduced during an oxidation step of a H-phosphonate. Only nucleophilic amines could be used by using this synthesis strategy. This results in a nitrogen atom which is protonated under acidic conditions which results in hydrolysis. Stereoselective synthesis is not disclosed in this context Acceptor-substituted amines could not be used since they are not nucleophilic and will not react with the dichlorophosphonate intermediate.

The P—N bond in standard phosphoramidates is known to be labile (Tomasz, J., and Ludwig, J., Nucleosides & Nucleotides 3(1) (1984) 45-60), especially under slightly acid conditions. Baschang, G., and Kvita, V., Angew. Chem. 85(1) (1973) 43-44 describe the reaction of a nucleotide phosphoric acid triester with azides such as methylsulfonyl azide to prepare tri-alkyl(aryl)imidophosphates which are, however, unstable and decompose.

Nielsen, J., and Caruthers, M. H., J. Am. Chem. Soc. 110 (1988) 6275-6276 describe the reaction of deoxynucleoside phosphites provided with a 2-cyano-1,1-dimethylethyl protective group in the presence of alkyl azide. Furthermore, the authors suggest that this principle is suitable for preparing nucleotides that are modified on the phosphate residue without elucidating which types of modifications prepared with the aid of the disclosed method could have particular advantages. In particular the authors suggest the introduction of alkyl residues.

Therefore it was one object of the invention to provide compounds with a stabilized phosphoamidate linkage.

It was a further object of the invention to provide a new and simple preparative approach to generate a plurality of different individual oligomers consisting of a defined sequence of selected monomeric units, whereas the stereochemistry of the monomeric units is defined.

The monomeric units themselves are build of two parts, a phosphoramidate containing part and a spacer part. The monomeric units themselves contain two groups R1 and R2 where R1 is connected to the phosphoramidate containing part and R2 is connected to the spacer part of the monomeric unit.

SUMMARY OF THE INVENTION

The trivalent phosphorous atom of a compound is reacted with a reagent in such a manner that a stable phosphate mimetic or a specifier is formed. Phosphoramidites with a phosphorous atom containing at least one hydroxyl residue which is provided with a protective group are reacted for this purpose with a free hydroxyl group: In the first synthesis cycle the hydroxyl group is linked to a solid support via a cleavable or non-cleavable linker. In further synthesis cycles the hydroxyl group is created by cleavage of the protective group from the growing oligomer. This results in formation of a phosphorous acid triester which is reacted with azides. By selecting suitable monomers for the synthesis which have a defined stereoconformation compounds of Formula 1 are produced in a stereocontrolled manner.

The objective was reached by a first embodiment of the invention, that is a chemical compound according to Formula 1,

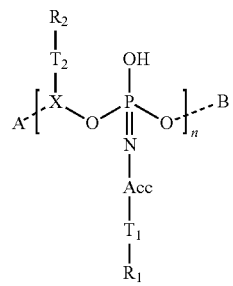

in which A is selected from the group consisting of
a hydroxyl group,
a phosphate, and
a C3-C10 monoalkyl phosphate (—O—P=O(O⁻)—O-alkyl), wherein said monoalkyl is linear, branched or a cycle and optionally substituted with a moiety selected from the group consisting of a detectable moiety and a reactive group selected from —SH, —NH$_2$, —O—NH$_2$, —NH—NH$_2$, —C(=O)H, —COOH, —CH=CH$_2$, —C≡CH, and —OH;

in which B is selected independently from A and is selected from the group consisting of
a hydrogen atom, and
a C3-C10 alkyl, wherein said alkyl is linear, branched or a cycle, and optionally substituted with a moiety selected from the group consisting of a detectable moiety and reactive functional group selected from —SH, —NH$_2$, —O—NH$_2$, —NH—NH$_2$, —C(=O)H, —COOH, —CH=CH$_2$, —C≡CH, —OH, and a solid support;

in which n is an integer denoting the number of monomers, and n is equal to or higher than 2;

in which for each monomer Acc, R1, R2, T1, T2 and X are selected independently from each other and from the Acc, R1, R2, T1, T2 and X moieties of the other monomer(s);

in which Acc is an electron acceptor selected from the group consisting of
- a methyl-sulfonyl,
- a C6-C10 aryl-sulfonyl,
- a C5-C6 heteroaryl-sulfonyl with 1 or 2 heteroatoms selected from N, O, and S,
- a C5-C10 cycloalkyl-sulfonyl,
- an electron-deficient 6 membered aromatic ring, and
- a six-membered heterocycle with at least one alkylated N-atom in ortho- or para-position, said heterocycle being selected from the group consisting of pyridinium, pyrimidinium and chinolinium;

in which X is a spacer part consisting of 2-16 atoms, whereby the spacer part is selected from the group consisting of
- a branched or linear C1-C6 alkyl,
- a linear C4-C14 heteroalkyl with one N atom
- a branched or linear C4-C14 alkenyl,
- a branched or linear C4-C14 alkinyl,
- a bis-(C1-C3)-alkyl-(C6-C10)-aryl,
- a bis-(C1-C3)-alkyl-heteroaryl, with 5-6 membered heteroaryl with 1-3 heteroatoms selected from N, O and S
- a 5-10 membered cycloalkyl
- a 5-10 membered heteroalkyl structure with 2 heteroatoms, whereby each heteroatom is independently selected from N, O, and S, and
- a 5-10 membered cyclo-heteroalkyl structure with 1-5 heteroatoms, whereby each heteroatom is independently selected from N, O, and S;

in which the atom or atoms of X which are connected to phosphoramidate or A are $sp^3$ C atoms;

in which R1 is selected independently from R2, and R1 is directly or via a tether T1 attached to Acc;

in which R2 is selected independently from R1, and R2 is directly or via a tether T2 to a C atom or (if present) N atom of X;

in which R1 and R2 are selected from the group consisting of
- a hydrogen atom,
- a core moiety selected from the group consisting of
  - a linear or branched C1-C6 alkyl group,
  - a linear or branched C2-C6 alkenyl group,
  - a linear or branched C2-C6 alkinyl group,
  - a 5-10 membered cycloalkyl group,
  - a 6-10 membered aryl group,
  - a 5-10 membered heterocyclic group with 1-5 heteroatoms, whereby each heteroatom is independently selected from N, O, and S,
- a substituent attached to the core moiety, whereby the substituent is selected from the group consisting of
  - a hydrogen atom,
  - a halogen atom,
  - a carboxyl group,
  - a formyl group,
  - a C1-C6 acyl group,
  - a C6-C10 aroyl group,
  - a hydroxyl group,
  - a C1-C6 acylamino group,
  - an amino group,
  - a carboxamido group,
  - a C1-C6 alkylmercapto group,
  - a cyano group,
  - a nitro group,
  - a C1-C6 alkoxy group,
  - a C1-C6 alkoxycarbonyl group,
  - a C6-C10 aryloxy group,
  - a C6-C10 aryloxycarbonyl group,
  - a sulfhydryl group,
  - a C6-C10 aryl- or C1-C6 alkyl-sulfonyl group,
  - a phosphatyl group,
  - a guanidyl group,
  - a primary or secondary C1-C6 carboxamido group,
  - a detectable moiety,
  - a C6-C10 aryl group,
  - a C2-C6 alkenyl group,
  - a C2-C6 alkinyl group, and
  - a 5-10 membered heteroaryl group, in which the tethers T1 and T2 are selected independently from each other, and a tether consists of a linear, branched or cyclic organic moiety comprising 1-30 C-atoms and 0-5 heteroatoms selected from N, O, and S, and 1-3 subunits selected from a carboxy moiety, an amide moiety and a urea moiety, whereby the internal heteroatoms with the exception of a disulfide bond are separated from each other by a minimum of two carbon atoms;

in which for each monomer X, R1 and R2, and T1 and T2 are selected independently from X, R1 and R2, and T1 and T2 from other monomers, whereby the compound of Formula 1 is a defined stereoisomer.

The invention also encompasses the salts of the compounds of Formula 1. A preferred counter ion is selected from the group consisting of $Li^+$, $Na^+$, $K^+$, $Mg^{++}$, $NH_4^+$, $N-alkyl_4^+$, and polyalkylamino-polycations.

A further embodiment of the invention is a process for producing a compound according to claim 1, comprising the steps (a) providing a solid support to which is attached a hydroxyalkyl group via a cleavable or non-cleavable linker, (b) providing a first compound according to Formula 2

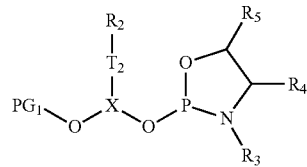

in which X is a spacer part consisting of 2-16 atoms, whereby the spacer part is selected from the group consisting of
- branched or linear alkyl,
- linear C4-C14 heteroalkyl with one N atom
- branched or linear C4-C14 alkenyl,
- branched or linear C4-C14 alkinyl,
- bis-(C1-C3)-alkyl-(C6-C10)-aryl,
- bis-(C1-C3)-alkyl-heteroaryl, with 5-6 membered heteroaryl with 1-3 heteroatoms selected from N, O and S
- 5-10 membered cycloalkyl
- 5-10 membered heteroalkyl structure with 2 heteroatoms, whereby each heteroatom is independently selected from the group consisting of N, O, and S,
- 5-10 membered cyclo-heteroalkyl structure with 1-5 heteroatoms, whereby each heteroatom is independently selected from the group consisting of N, O, and S;

in which the atom or atoms of X which are connected to phosphoramidate are sp³ C atoms;
in which R2 in the monomer is a moiety selected from the group consisting of
a hydrogen atom,
a core moiety selected from the group consisting of
a linear or branched C1-C6 alkyl group,
a linear or branched C2-C6 alkenyl group,
a linear or branched C2-C6 alkinyl group,
a 5-10 membered cycloalkyl group,
a 6-10 membered aryl group,
a 5-10 membered heterocyclic group with 1-5 heteroatoms, whereby each heteroatom is independently selected from N, O, and S;
a substituent attached to the core moiety, whereby the substituent is selected from the group consisting of
a hydrogen atom,
a halogen atom,
a protected carboxyl group,
a protected formyl group,
a C1-C6 acyl group,
a C6-C10 aroyl group,
a protected hydroxyl group,
a C1-C6 acylamino group,
a protected amino group,
a carboxamido group,
a C1-C6 alkylmercapto group,
a cyano group,
a nitro group,
a C1-C6 alkoxy group,
a C1-C6 alkoxycarbonyl group,
a C6-C10 aryloxy group,
a C6-C10 aryloxycarbonyl group,
a protected sulfhydryl group,
a C6-C10 aryl- or C1-C6 alkyl-sulfonyl group,
a protected phosphatyl group,
a guanidyl group,
a primary or secondary C1-C6 carboxamido group,
a detectable moiety,
a C6-C10 aryl group,
a C2-C6 alkenyl group,
a C2-C6 alkinyl group,
a 5-10 membered heteroaryl group;
in which T2 in the monomer is a tether consisting of a linear, branched or cyclic organic moiety comprising 1-30 C—atoms and 0-5 heteroatoms selected from N, O, and S, and 1-3 subunits selected from a carboxy moiety, an amide moiety and a urea moiety, whereby the internal heteroatoms with the exception of a disulfide bond are separated from each other by a minimum of two carbon atoms;
in which
R3 is selected from a first group of substituents consisting of H, C1-C3-alkyl, or
R3 is selected from a second group of substituents consisting of acetyl, monofluor-acetyl, and difluoracetyl;
in which R4 is selected from the group consisting of H, C1-C3 alkyl, and C6-C10 aryl;
in which R3 and R4 are optionally covalently connected to form a —(CH₂)$_n$-bridge with n=3 or n=4;
in which R5 is selected from the group consisting of H, C1-C3 alkyl, and C6-C10 aryl; and
in which PG1 is either a photo-cleavable linker selected from the group consisting of NVOC and NPPOC, or PG1 is an acid-cleavable linker selected from the group consisting of monomethoxytrityl, dimethoxytrityl, trimethoxytrityl, 9-phenylxanthine-9-yl (Pixyl), and 9-(p-methoxyphenyl)xanthine-9-yl (MOX);
(c) in case that R3 consists of the first group of substituents or in case R3 is covalently linked to R4
performing the step of activating the compound of step (b) with an activator selected from
1H-tetrazole, dicyano-imidazole,
N-phenylimidazolium triflate, N-methylbenzimidazolium triflate, and
N-(cyanomethyl)pyrrolidinium triflate,
or in case R3 consists of the second group of substituents
performing the step of activating the compound of step (b) with N,N,N',N'-tetramethylguanidine
thereby providing an activated compound;
(d) reacting the activated compound of step (c) with the hydroxyl group of step (a), thereby forming a phosphate triester,
whereby in the case of R3 being selected from the first group a beta-amino function with R6=H is formed, and
whereby in the case of R3 being selected from the second group an acylated beta-amino function is formed;
(e) in case that R3 consists of the first group of substituents, performing the step of capping the beta amino group of step (d) with acetanhydride thereby introducing R6=acetyl, and proceeding with step (f), otherwise directly proceeding with step (f);
(f) reacting the capped compound of step (e) or the compound of step (d) with a compound of Formula 3

in which R1 is selected independently from R2 and R1 is selected from the group consisting of
a hydrogen atom,
a halogen atom,
a protected carboxyl group,
a protected formyl group,
a C1-C6 acyl group,
a C6-C10 aroyl group,
a protected hydroxyl group,
a C1-C6 acylamino group,
a protected amino group,
a carboxamido group,
a C1-C6 alkylmercapto group,
a cyano group,
a nitro group,
a C1-C6 alkoxy group,
a C1-C6 alkoxycarbonyl group,
a C6-C10 aryloxy group,
a C6-C10 aryloxycarbonyl group,
a protected sulfhydryl group,
a C6-C10 aryl- or C1-C6 alkyl-sulfonyl group,
a protected phosphatyl group,
a guanidyl group,
a primary or secondary C1-C6 carboxamido group, a detectable moiety,
a C6-C10 aryl group,
a C2-C6 alkenyl group,
a C2-C6 alkinyl group,
a 5-10 membered heteroaryl group,
in which T1 is a further tether and is selected independently from T2, and T1 is selected from the group consisting of a linear, branched or cyclic organic moiety comprising 1-30 C— atoms and 0-5 heteroatoms selected from N, O, and S, and 1-3 subunits selected from a carboxy moiety, an amide moiety and a urea moiety, whereby the internal heteroatoms with the exception of a disulfide bond are separated from each other by a minimum of two carbon atoms,
in which Acc is an electron acceptor selected from the group consisting of
a methyl-sulfonyl,
a C6-C10 aryl-sulfonyl,
a C5-C6 heteroaryl-sulfonyl with 1 or 2 heteroatoms selected from N, O, and S,
a C5-C10 cycloalkyl-sulfonyl,
a 6 membered electron-deficient aromatic ring, and
a six-membered heterocycle with at least one alkylated N-atom in ortho- or para-position, said heterocycle being selected from the group consisting of pyridinium, pyrimidinium and chinolinium;
thereby forming a protected and immobilized monomer;
(g) capping the non-reacted free hydroxyl groups of the solid support with acetanhydride or pivaloylanhydride;
(h) in case PG1 is a photo-cleavable protective group removing PG1 by applying UV light to the protected and immobilized monomer, or in case PG1 is an acid-labile protective group removing PG1 by applying acidic conditions to the protected and immobilized monomer,
whereby on the immobilized monomer a new free hydroxyl group is formed
(i) providing a further compound according to Formula 2, whereby R2, R3, R4, R5, T2, PG1 and X are selected independently from each other and independently from the respective R2, R3, R4, R5, T2, PG1 and X in each other monomer,
and in case that R3 consists of the first group of substituents
or in the case R3 is covalently linked to R4
performing the step of activating the compound of step (b) with an activator selected from 1H-tetrazole, dicyano-imidazole, N-phenylimidazolium triflate, N-methylbenzimidazolium triflate, and N-(cyanomethyl)pyrrolidinium triflate,
or in case R3 consists of the second group of substituents
performing the step of activating the compound of step (b) with N,N,N',N'-tetramethylguanidine,
thereby providing an activated further compound;
(k) reacting the free hydroxyl group formed during step (h) with the activated compound of step (i) thereby forming a phosphate triester,
whereby in the case of R3 being selected from the first group a beta-amino function with R6=H is formed and
whereby in the case of R3 being selected from the second group an acylated beta-amino function is formed;
(l) capping the beta amino group of step (k) with acetanhydride in case that R3 consists of the first group of substituents, thereby introducing R6=acetyl, and proceeding with step (m),
otherwise directly proceeding with step (m);
(m) reacting the compound of step (e) or the compound of step (d) with a further compound of Formula 3

whereby Acc, R1 and T1 are selected independently from each other and independently from Acc, R1 and T1 of the other monomer(s),
thereby forming a protected and immobilized oligomer with a further monomer;
(n) capping free hydroxyl groups with acetanhydride or pivaloylanhydride;
(o) in case PG1 is a photo-cleavable protective group removing PG1 by applying UV light to the protected and immobilized monomer, or in case PG1 is an acid-labile protective group removing PG1 by applying acidic conditions to the protected and immobilized monomer
whereby a new free hydroxyl group is formed
(p) repeating steps (i) to (o) z times, whereby z is an integer between 0 and 8
(q) cleavage of the permanent protective groups of the phosphoramidate moieties and the protective groups attached to R1 and R2 under basic conditions or under reducing conditions,
whereby in the case of the presence in step (a) of a cleavable linker to the solid support the linker is cleaved,
thereby obtaining a compound according to Formula 1

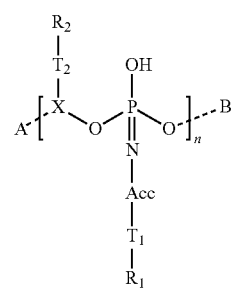

(Formula 1)

with A=OH,
with B=H, and
n=z-2;
and in case of the presence of a non-cleavable linker in step (a) obtaining a compound according to Formula 1 attached to the solid support

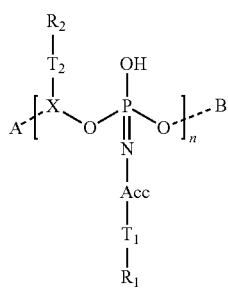

(Formula 1)

with A=OH,
with B=non-cleavable linker attached to the solid support
and n=z−2.

Further embodiments of the invention are oligophosphoramidates obtainable by the process according to the invention.

BRIEF DESCRIPTION OF THE FIGURES

Note: Any roman numeral used to indicate a particular Formula refers to the same Formula with a corresponding arabic numeral. E.g. Formula III=FORMULA III=Formula 3.

DETAILED DESCRIPTION OF THE INVENTION

Figure 1:
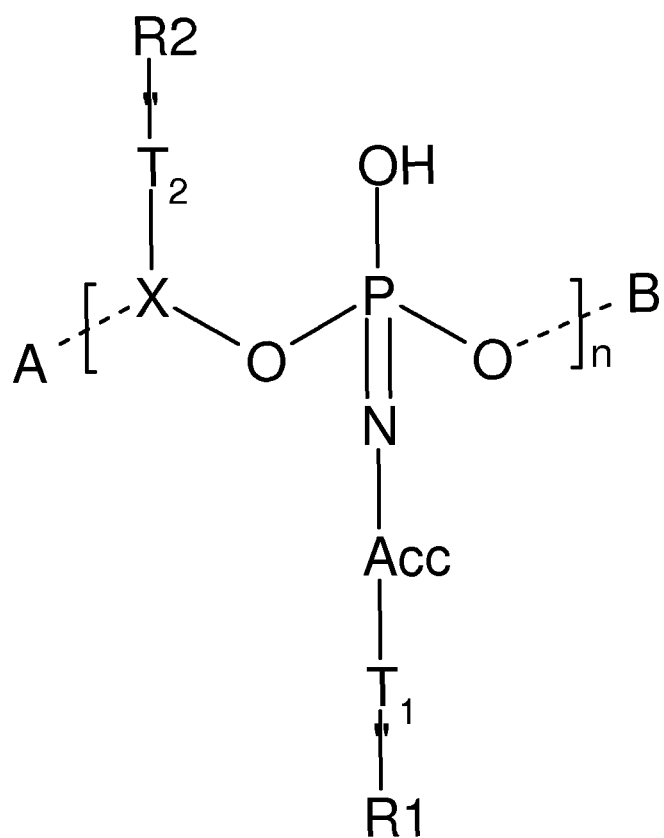
FIG. 1: The structure of Formula 1
Figure 2:
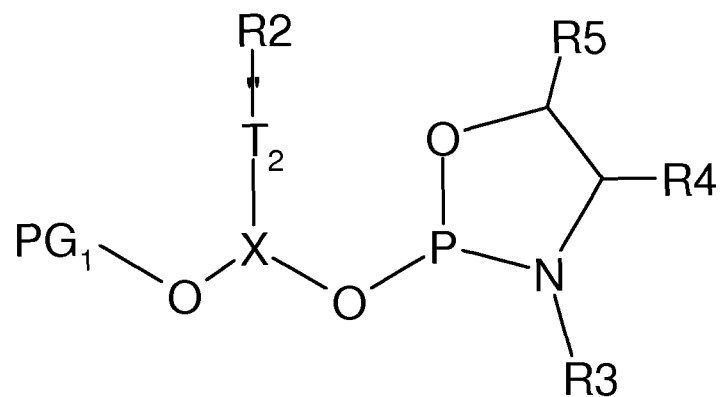
FIG. 2: The structure of Formula 2
Figure 3:
FIG. 3: The structure of Formula 3
Figure 4:
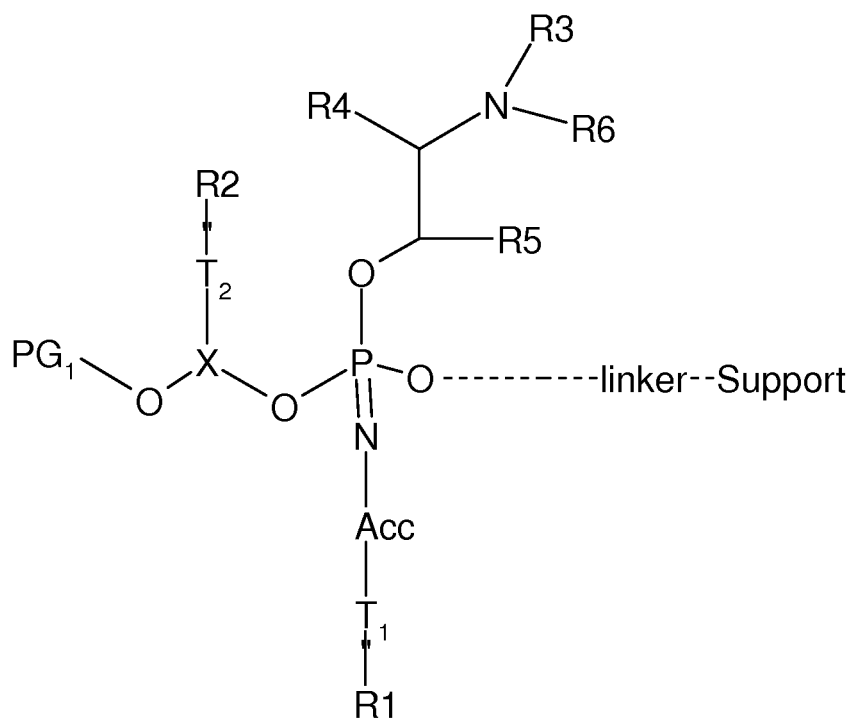
FIG. 4: The structure of Formula 4

Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a term is first defined by any of the definitions set forth in this description of the present invention.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range "between" n1 and n2 is given by n1≤x≤n2. Thus, the expression is equivalent to the value x in the range of n1 to n2.

If not stated otherwise, it is understood that the term "about" in combination with a numerical value n indicates a value x in the interval given by the numerical value ±5% of the value, i.e. n−0.05*n≤x≤n+0.05*n. In case the term "about" in combination with a numerical value n describes a preferred embodiment of the invention, the value of n is most preferred, if not indicated otherwise.

A "stereoisomer" is a molecule of which one or more isomers exist and such isomeric molecules have the same molecular formula and sequence of bonded atoms (constitution), but which differ in the three dimensional orientations of their atoms in space. By way of example, enantiomers are two stereoisomers that are related to each other in that they are mirror images of each other, which are non-superimposable. As another example and in contrast to enantiomers, "diastereomers" are stereoisomers not related through a reflection operation as in the case of enantiomers. Diastereomers are not mirror images of each other. Diastereomers include meso compounds, cis-trans (E-Z) isomers, and non-enantiomeric optical isomers. "Conformational isomerism" is a form of isomerism that describes the phenomenon of molecules with the same structural formula having different shapes due to rotations about one or more bonds. Different conformations can have different energies and can usually interconvert.

The term "stereocontrolled synthesis" is related to a method where conditions and kind of phosphoramidite monomers are chosen in such a way that one stereoisomer is produced in excess compared to all other stereoisomers. Preferably the desired product is formed in more than 80% especially preferred in more than 90%.

A detectable moiety is understood to denote substances which can be detected with the aid of analytical methods. They can for example be units that can be detected by mass spectroscopy, immunologically (e.g. for digoxigenin as detectable moiety), using specific binding proteins such as avidin, streptavidin or derivatives thereof (for biotin as detectable moiety) or with the aid of NMR (e.g. 13-C or fluoro-containing residues as detectable moiety) or by ESR (e.g. spin labels like TEMPO as detectable moiety). Another class of detectable moieties are detected by electrochemical methods, e.g. metal complexes like ferrocene or redoxactive organic compounds like phenazine methosulfate.

Preferred detectable units in particular include substances that can be detected by optical methods such as fluorescence and UV/VIS spectroscopy such as azodyes, triphenylmethan dyes, coumarines, pyrene, perylene, fluoresceins, rhodamines, cyanines, merocyanines, oxazines or labels which could be detected by Raman spectroscopy labels like benzotriazoles and substituted phenyl residues. The detectable moiety can also comprise a plurality of one selected label e.g. within a dendrimer, or a combination of fluorescent labels which are capable of interacting by fluorescene resonance energy transfer.

Another group of preferred detectable moieties are detectable particles like gold nanoparticles, magnetic quantum dots, silicate particles which contain lanthanides oxides or latex particles with incorporated dyes, or zeolithes with incorporated dyes.

In the case that the detectable moiety comprises groups which are not compatible with the synthesis protocol the detectable moiety is protected with a permanent protecting group one well known example is bis pivaloyl fluorescein.

An important goal pursued by the present invention was to provide advantageous compounds and conditions for synthesizing oligomers (or polymers) from monomeric building blocks. The envisaged oligomers should on the one hand be suited for use as mimetics or specifiers of biomolecules selected from the group consisting of peptides, proteins, polysaccharides, and lipids, as well as conjugates thereof). Preferably, the envisaged mimetics could advantageously be used for imitating one or more properties of certain biomolecules, either in vitro or in vivo. On the other hand there is the concept according to the invention of synthesizing oligomers in a way to facilitate specific interaction of an oligomer with a target biomolecule.

A general example for specific interactions among biomolecules is the binding of a ligand by a receptor. Particular examples are the interactions of an antibody with an antigen and a lectin with a polysaccharide. A compound according to the invention which is capable of interacting in a similar way with a target molecule is also referred to as a "specifier" molecule or compound.

It was a rationale of the present invention that specific interaction of a chemically synthesized compound with a target molecule requires an arrangement of functional groups which are capable of interacting with a target molecule or a portion thereof. Possible interactions are non-covalent interactions such as hydrogen bonding, ionic- and van der Waals-type of interactions. Other ways to interact can also be envisaged, e.g. a formation of a complex.

Given a target molecule with a defined structure and three-dimensional conformation, synthesis of a specifier compound with a specific arrangement of functional groups can be complicated in case stereoisomers arise from the synthesis of the specifier compound. The specifier molecule according to the invention preferably is an oligomer composed of two or more monomers.

Problems due to the occurrence of stereoisomers are thus even more the case in oligomeric compounds in which each monomer comprises one or more atoms which already are stereocenters or in cases when they become stereocenters in the course of a synthesis scheme. In some cases this problem can be partly alleviated by selecting specific S- or R-compounds as educts. However, this is not always possible. In particular, phosphoramidite monomers pose a significant challenge in view of the P atom which arises as a stereocenter upon formation of phosphoramidites.

Specifier molecules are desired which are characterized by a specific structure and three-dimensional conformation. This very importantly includes the provision of one or more stereocenters with predetermined, i.e. defined conformation. Therefore, a particular object of the invention was to provide not only a new and simple preparative approach to generate a plurality of different individual oligomers consisting of a defined sequence of selected monomeric units, but also a means to control the stereochemistry of the monomeric units. As the monomeric units according to the invention comprise a phosphoramidate entity, control of the stereochemistry concerning the P-atoms was a particular objective.

Figure 5:
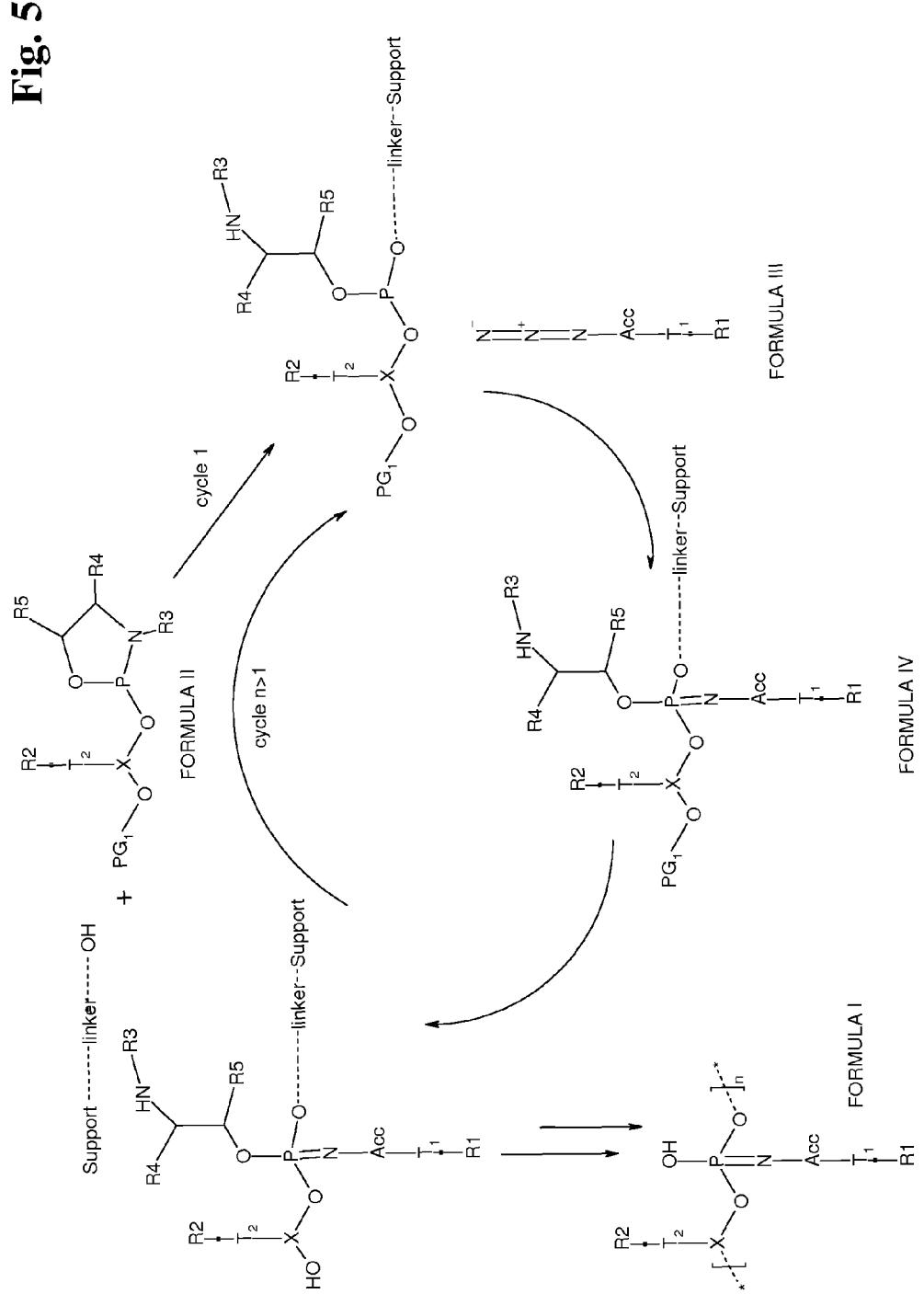
FIG. 5: Scheme depicting the cycle of synthesis, capping steps excluded for simplicity

A further central idea of the present invention was in this connection to start with a compound comprising a trivalent phosphorus atom and to react the trivalent phosphorous atom with a reagent in such a manner that a stable phosphate mimetic is formed as shown in FIG. 5 (capping steps are not included). According to the invention the phosphoramidites according to Formula 2 with a phosphorus atom containing at least one hydroxyl residue which is provided with a protective group are reacted in the presence of an activator for this purpose with a free hydroxyl group: In the first synthesis cycle the hydroxyl group is linked to a solid support via a cleavable or non cleavable linker. In further synthesis cycles the hydroxyl group is created by cleavage of the protective group PG1 from the growing oligomer. This results in formation of a phosphorous acid triester which is reacted with the azides according to Formula 3 having the structure N=N=N-Acc-T1-R1 in which Acc is an electron acceptor. Acc itself is substituted with a residue R1 and R1 can be selected from a wide range of organic substituents. Between Acc and R1 a tether moiety T1 may also be present. The reaction of the phosphitetriester with the acceptor substituted azid a P(V) stereocenter is created. In order to control stereochemistry which means that the Rp or Sp isomer is preferably formed pure P(III) epimers which comprise a chiral auxiliary are used in the subsequent coupling reaction. Alternatively activators which are modified with bulky chiral auxiliaries could be used in combination with standard phosphoramidites. Another less suitable alternative is to use purified P(V) monomers where the stereochemistry on the P is defined. In each case if the monomers according to Formula 2 comprise further stereocenters beside the P(III) stereocenter the stereochemistry of all other stereocenters is defined, too. After completing all synthesis cycles, protective groups PG2 and further protecting groups which are attached if necessary to R1 and R2 are cleaved off. This results in the formation of the compounds of Formula 1 with a pentavalent phosphorus atom to which a strongly electron-attracting electron acceptor group is covalently bound via an N-atom. This molecular assembly ensures that the compounds produced in this manner are stabilized and are therefore less susceptible to acid hydrolysis, in contrast to the phosphoramidate compounds known from the prior art.

This idea underlying the invention can be applied to all processes in which a trivalent phosphorus is formed as an intermediate.

Phosphoramidites comprising the substituted spacer unit, to which a protected hydroxyl group (e.g. dimethoxytrityl protected) is attached are useful starting materials to introduce a monomeric unit during solid phase synthesis of a oligophosphoamidate. Phosphoramidites are activated by a weak acid, e.g. tetrazol or dicyanoimidazol, and than reacted with a hydroxyl group of a monomeric unit which is already attached either via a cleavable or non cleavable linker to a solid support. This results in formation of phosphoric acid triesters with a trivalent phosphorus atom as intermediate products, whereas one of the phosphoric ester bonds is linked to the monomeric unit which was attached to the solid support, and the second bond is linked to the monomeric unit which is to be attached. The phosphorus atom is linked to a protected hydroxyl group such as for example to a beta-cyanoethyloxy group via the third ester bond. Since this reaction could in principle result in two P-stereoisomers, the stereochemistry is controlled either by using phosphoramidite which are pure P-diastereomers or by using a activator which is modified with bulky chiral auxiliary. According to the invention this intermediate was reacted with an appropriate azide in the process of which the trivalent phosphorus atom is oxidized to a pentavalent atom by covalently linking —N-Acc-R1 to the phosphorus atom while releasing nitrogen. Oligophosphoamidate synthesis can then be subsequently continued by releasing the protective group (e.g. dimethoxytrityl) from the newly attached monomeric unit and reacting with a further phosphoramidite. After the desired product was synthesized the oligomer is cleaved from the solid support, e.g. by ammonia. During the cleavage process preferably all other protecting groups are removed, too. Stable polyphosphoramidates are obtained as end product which are modified in almost any manner on one or more phosphoramidate residues and on the spacer units linking the phosphoamidate moieties. If the first hydroxyl group is attached to the support via a noncleavable linker the protective groups are removed as described above but the oligophosphoamidate remains attached to the solid support. Notably, this is useful for preparation of arrays of oligophosphoamidates.

Within the scope of the present invention some of the terms used are defined as follows:

The term protective group (or protecting group) denotes molecular assemblies which are connected to one or more functional groups of a molecule such that, as part of a multi-step synthesis reaction, only one particular, non-protected functional group can react with the desired reaction partner. The skilled person differentiates between permanent and temporary protective groups. The first protects the side chains and the phosphoramidate of the growing oligomer until the synthesis is finalized; the second protects the growing chain end of the oligomer and is removed before each prolongation step. It is reintroduced with the incorporation of the next monomer. Generally, the use of one or more protective groups assures that oligomer synthesis proceeds in the desired way.

Examples of frequently used protective groups to protect hydroxyl groups are trityl, monomethoxytrityl, dimethoxytrityl, trimethoxytrityl, trialkylsilyl, allyl, 9-phenylxanthine-9-yl (Pixyl) and 9-(p-methoxyphenyl)xanthine-9-yl (MOX), NVOC, NPPOC, beta-cyano-ethyl and others which are known to the skilled person. Protective groups for protecting amino groups are trifluoroacetyl, BOC, benzyloxycarbonyl, Fmoc and others. Other possible protective groups are summarized in standard text books (Greene, T., W., Protective groups in organic synthesis, John Wiley&Sons, Inc. (1981) New York, Chichester, Brisbane, Toronto; Sonveaux, E., Methods in Molecular biology, Protocols for Oligonucleotide conjugates, Humana Press, Totowa, N.J., Vol. 26 (1994), Chapter 1, p. 1-71).

The term spacer denotes the linkage between two phosphoramidate moieties. A spacer usually contains a characterizing substituent. The spacer is a trifunctional moiety where two of the arms are connected to the O-atoms of the adjacent phosphoamidates when an oligomer is formed. The third arm of the spacer contains a substituent from the group defined below. It may be a branched alkyl, heteroalkyl (an alkyl residue which additionally comprises one or more N atoms), alkenyl, alkinyl, aryl, heteroaryl, cycloalkyl or cyclo-heteroalkyl structure with three connectivities. Between the substituent and this branched structure a tether is optionally incorporated. If the spacer is located terminally, or in a monomer of the compound of the invention, one O-atom and/or the spacer is linked to a hydrogen, to a solid phase (optionally via a linker), to a detectable moiety or to phosphate or phosphoramidate to which a reactive group like —SH, —NH$_2$, —O—NH$_2$, —NH—NH$_2$, —C(=O)H, —COOH, —(CH=CH)$_2$—, —C≡CH, —OH or a phosphate is attached via a linear, branched or cyclic C3-C18 alkyl group. For introducing such groups via a phosphate or phosphoramidate group to the oligomer standard 5' modifier phosphoramidites, internal modifier phosphoramidites or specially modified solid supports are used. Such modifiers are well known since they are frequently used for modifications of oligonucleotides. A wide variety of such modifiers are commercially available and are subject of standard textbooks and reviews, e.g. Wojczewski, C., et al., Synlett, No. 10 (1999) 1667-1678; Meyer, R. B. jun., Methods in Molecular biology, Protocols for Oligonucleotide conjugates, Humana Press, Totowa, N.J., Vol. 26 (1994), Chapter 2, p. 73-91; Agrawal, S., Methods in Molecular biology, Protocols for Oligonucleotide conjugates, Humana Press, Totowa, N.J., Vol. 26 (1994), Chapter 3, p. 93-120; Fidanza, J. A., et al., Methods in Molecular biology, Protocols for Oligonucleotide conjugates, Humana Press, Totowa, N.J., Vol. 26 (1994), Chapter 4, p. 121-143; Chu, B. C. F., and Orgel, L. E., Methods in Molecular biology, Protocols for Oligonucleotide conjugates, Humana Press, Totowa, N.J., Vol. 26 (1994), Chapter 5, p. 145-165; Ranasinghe, R. T., and Brown, T., et al., Chem Commun 44 (2005) 5487-5502; as well as Grasby, J. A., and Williams, D. M., Organophosphorus Chemistry 29 (1999) 161-230.

"Reactive group" refers to groups of a molecule which are able to react under suitable conditions with another molecule while forming a covalent bond. Examples of reactive groups are hydroxyl groups, amino groups, thiol, hydrazino, hydroxylamino, diene, alkine and carboxylic acid groups.

Reactive groups are used to conjugate the oligophosphoramidate after cleaving from the solid support to a nanoparticle or to an biomolecule like proteins, carbohydrates, oligonucleotides and lipids. Reactive groups are preferably selected in such a manner that the reactivity of the reactive groups involved in conjugation reaction is orthogonal to other reactive groups which are present in the oligophosphoramidate. Preferred are therefore alkin, diene groups which can react with azides or dienophile.

Phosphoramidites are molecules containing a trivalent phosphorus atom which can be coupled to a hydroxyl group. An example is beta-cyanoethyl-bis-diisopropylamino-phosphoramidite which is very well known from standard oligonucleotide synthesis.

One basic requirement is that all stereocenters of the phosphoramidites which are not altered during the assembly of monomers are predefined. Therefore the stereochemical conformations of the spacer, the thether moiety and the substituents can be defined.

Especially useful and preferred are phosphoramidites which do not have a stereocenter in the spacer part like unsubstituted linear alkyl groups like propyl (see EP 1 186 613) or dialkyl aryl spacers like p-bismethylphenylen or 1,3,5 substituted benzene moieties (Behrens, C., and Dahl, O., Nucleosides & Nucleotides 18(2) (1999) 291-305) or like bis hydroxyl ethylamin with a further substitutent on the N atom (Korshun, V. A., et al., Synthetic Communications 26(13) (1996) 2531-2547).

Further especially useful and preferred are phosphoramidites which comprise a spacer part which is functionalized with two hydroxyl groups and a functional group whereby the stereochemical conformation is fixed. Examples are phosphoramidite derivatives of D or L-ribose eg 1' amino 2-deoxy D ribose or 1' β carboxy-2-deoxy D ribose Kawakami, J., et al, Chemistry Letters 33(12) (2004) 1554-1555, of D or L threoninol (WO 92/02532), derivatives of 1 hydroxy 2 hydroxymethyl 4-amino cyclopentan ("aminocarba2' deoxy ribose"), derivatives of mannitol (EP 1 431 297), and derivatives of pyrrolidine (WO 03/104249).

Also for synthetic reasons such derivatives are preferred since they comprise a primary and secondary hydroxyl groups, since this allows the selective protection of hydroxyl groups. The temporary protective group is preferably introduced at the primary hydroxyl group. The secondary hydroxyl group is transferred in the phosphoramidite and the functional group is used to attach substituents.

In order to get a high density of residues R1 and R2 spacer parts which link two phosphoramidates via 3 carbon atoms are preferred. In this case the spacing of residues is similar to the spacing in natural peptides.

P(V)-Chiral centers are formed during assembly of monomers. Stereocontrol during reacting of on phosphoramidite moiety with a free hydroxyl group could be achieved by using special phosphoramidites instead of the standard beta-cyanoethyl-bis-diisopropylamino-phosphoramidite. Such phosphoramidites have bulky chiral substituents on the P(III) atom. Examples are oxazaphospholidine monomers especially derived from ephedrine (WO 9637504) or from prolinol (Oka, N., et al., Nucleic Acids Symposium Series No. 52 (2008) 335-336; Hyodo, M., et al., Eur J. Org Chem (2005) 5216-5223) and N-acyl phosphoramidites (Wilk, A., et al., J. Am. Chem. Soc. 122(10) (2000) 2149-2156) derived from N fluoracetyl 8(+)2 amino 1 phenyl ethanol.

Activators are well known from oligo nucleotide synthesis and are used to activate the phosphoramidite in order to allow an efficient reaction with a hydroxyl group Standard activators like Tetrazole and derivatives thereof like Benzylthiotetrazol, DCI, can be used. Higher stereoselectivity is obtained with activators like N-methylbenzimidazolium triflate and N-phenylimidazolium triflate N-cyano methyl pyrrolidinium triflate (Hyodo, M., et al., Eur J. Org Chem (2005) 5216-5223). Acyl phosphoramidites require activation with N,N,N',N'-Tetramethylguanidin (Wilk, A., et al., J. Am. Chem. Soc. 122(10) (2000) 2149-2156).

The term "cleavable linker" is related to a linker between the solid support and the synthesized oligophoshoramidates. The cleavable linker is inert towards conditions which are used during synthesis, but the cleavable linker is cleaved after the synthesis is completed which results in release of the oligophosphoramidate from the solid support. A variety of cleavable linkers are known in literature (Ghosh, P. K., et al., J. Indian Chem. Soc. 75 (1998) 206-218). Preferred cleavable linkers are succinyl and oxalyl linkers. Another class of well known cleavable linkers are used in combination with succinyl linkers in order to get a terminal phosphate or phosphoramidate groups eg 2-[2-(4,4'-Dimethoxytrityloxy)ethylsulfonyl]ethyl-2-succinoyl)-linker.

The term "non cleavable linker" refers to a chemical entity which is attached to a solid surface and is inert towards conditions which are used during and after oligomer synthesis. Preferred "non cleavable linkers" are linear C6-C40 alkyl linkers, or oligoethylenglycol linkers with 3-10 ethylenglycol subunits or oligopropylphosphodieesters with 3-10 O—$(CH_2)_3$—O—$P(O)_2$-subunits.

The term "solid support" refers to controlled pore glass particle or polystyrene bead, a glass slide a plastic slide, a glass bead or a silica particle or a semiconductive chip.

Preferably controlled pore glass modified with an aminoalkyl silane is used in combination with cleavable linkers.

Glass surfaces which could be flat or porous modified with hydroxyalkyl silanes or hydroxyl alkyl(polyethylenoxy)silanes are used as support with a non cleavable linker. The oligophosphoramidate is than directly synthesized on the O of the hydroxyalkyl silanes or O—$(CH_2)_3$—O—$P(O)_2$-spacers are introduced by using standard oligonucleotide synthesis protocols with several couplings of 3-(4,4'-Dimethoxytrityloxy)propyl-1-[(2-cyanoethyl)-(N,N-diisopropyl)]-phosphoramidite prior to synthesis of the oligophosphoramidate.

The term "electron acceptor" encompasses atomic structures which have the tendency to attract free electron pairs. One measure of this is the Hammett constant. A "Hammett constant" or "Hammett substituent constant" is explained by the Hammett equation, generally admitted in organic chemistry. The Hammett equation describes a linear free-energy relationship relating reaction rates and equilibrium constants for many reactions with two parameters: a substituent constant and a reaction constant. The basic idea is that for any two reactions with two reactants only differing in the type of substituent the change in free energy of activation is proportional to the change in Gibbs free energy. Substituent constants obtained by the Hammett's rule include $\sigma_p$ and $\sigma_m$ values. These values are found in many general textbooks, for example, J. A. Dean (ed.), Lamge's Handbook of Chemistry, $12^{th}$ ed. MacGraw-Hill (1997).

The present invention concerns in particular embodiments in which the Hammett constant $\sigma_p$ exceeds a certain value of 0.30, preferably 0.45 and particularly preferably 0.60 (Hansch, C., et al., Chem. Rev. 91 (1991) 165-195).

The electron acceptor must additionally be compatible with all chemical reactions in oligophorphoramidate synthesis i.e.
- the electron acceptor should not be oxidized by iodine (i.e. the electron acceptor is inert towards oxidation by iodine),
- the electron acceptor must be inert towards acids, particularly towards dichloroacetic acid and trichloroacetic acid, and
- the electron acceptor must be inert towards bases, in particular towards ammonia, and
- the electron acceptor should not react with (i.e. the electron acceptor preferably is inert towards) trivalent phosphoramidates.

Examples of electron acceptors which fulfill these conditions are:
$SO_2$-alkyl (C1-C6 preferred), $SO_2$-aryl(C6-C10 preferred), and electron-deficient aromatic and heteroaromatic rings (6 membered preferred) like (but not limited to) pyridyl, pyridylium, pyridazyl, tetrafluorophenyl, benzotriazyl. In addition these acceptors can also be bound to the nitrogen atom in a vinylogous or phenylogous manner. In addition to these acceptors also nitro- and cyano-acceptors can be bound to the nitrogen atom in a vinylogous or phenylogous manner.

The term "substituted" means that the structure that is referred to as being substituted contains another residue at any position provided this position is not defined in more detail. The term "optionally substituted" denotes that the structure referred to in this manner comprises embodiments with and without an additional residue.

The term "six-membered $N^+$-heterocycle" encompasses N-heterocycles which are alkylated on an $sp^2$ nitrogen such that the overall charge of the heterocycle is positive. Examples of this are pyridinium, pyrimidinium and quinolinium. Such heterocycles (among others) are known in the art to be electron deficient.

A library of oligophosphoramidates according to the invention refers to a plurality of oligophosphoramidates where each member is different from another member of the library. Different means that the composition of monomers is different regarding the sequence of monomers and/or different regarding the chemical structure of a monomer.

A minimal library consist from more than 10 members; preferably a library has more than 1,000, most preferred more than 1 million members. Each member can be present in the library as one or more replicates whereby the replicates share the same chemical structure (that of the member). Preferably the number of replicates per member is higher than 10,000 most preferred higher than 100,000. Libraries may preferably also comprise one or more coding entity with which each member can be identified. A simple way for coding is a defined position which is realized in a an array of members whereby each member is synthesized or spotted on a flat surface on a exactly defined position, whereby per spot 100,000-1,000,000 replicates of a given member are immobilized via a noncleavable linker. Alternatively, each member is conjugated to a coding moiety which can be (preferred) selected from the group consisting of a color-coded bead, a DNA sequence, a mass tag and a Raman label.

Compounds of the invention are shown by Formula 1 above. In Formula 1, the bracketed portion is herein referred to as a monomeric unit. A monomeric unit is comprised of a spacer segment with a phosphoramidate attached thereto.

Compounds of the present invention are made up of at least 2 of these monomeric units. Included in a monomeric unit is a phosphoramidate moiety that, in turn, is capable of bearing functional groups thereon. The phosphoramidate moiety is covalently bonded to a spacer segment which may also be capable of including a variety of further functional groups covalently bonded thereto. Further functional groups are covalently bonded directly to the backbone segment and the phosphoramidate, or via an optional tether group.

The spacer segment and phosphoramidate moiety serve as sites for connecting certain other groups that impart "functional" properties to the oligomeric compounds of the invention. By varying these interactive or non-interactive functional groups-diversity is incorporated into the compounds of the invention.

The term tether (or linker) denotes a carbon chain having a length of 1-30 C— atoms or can also be a bisconnectable cyclic structure. A tether can also contain one or more internal heteroatom like nitrogen, oxygen, and/or sulphur and may thus comprise an amide or urea moieties. Tethers can also be branched, e.g. be dendritic. A tether interconnects a spacer or a phosphoramidite moiety with, e.g. a substituent, a functional group or a detectable unit which may optionally be protected by one or more protective groups. In the context of this invention, internal heteroatoms with the exception of a disulfide bond must be separated from each other by a minimum of two carbon atoms.

The groups R1 and R2 can be "interactive" or "non-interactive." By interactive, it is meant that they will interact with a target molecule in some manner (that need not but can be predefined). By non-interactive, it is meant that they are not designed to primarily interact with a target molecule, and in fact while they may interact with the target molecule, the primary purpose of the non-reactive moieties are to impart other properties to the molecule such as effecting uptake, distribution, metabolism or identification.

The interactive or non-interactive groups are attached to the spacer segment and phosphoramidate moiety with or without intervening tethers. Tethers, as used in the context of this invention, are bivalent or polyvalent groups such tethers can be used to position R1 and R2 in space with respect to the linear backbone or the phosphoramidate moiety of the oligomeric compound synthesized or to link R1 and/or R2 to the spacer or phosphoramidate moiety that themselves are for chemical reasons not bindable to the parts of the monomeric unit.

Aryl groups according to the invention include but are not limited to substituted and unsubstituted aromatic hydrocarbyl groups such as phenyl and naphthyl groups. Aralkyl groups include but are not limited to groups having both aryl and alkyl functionality, such as benzyl and xylyl groups.

A number of functional groups can be introduced into compounds of the invention containing protective groups.

Solid supports useful for synthesis of compounds according to the invention include controlled pore glass (CPG), oxalyl-controlled pore glass (see, e.g., Alul, R. H., et al., Nucleic Acids Research 19(7) (1991) 1527-1532), TentaGel Support—an aminopolyethyleneglycol derivatized support (see, e.g., Wright, P., et al., Tetrahedron Letters 34(21) (1993) 3373-3376) or Poros—a copolymer of polystyrene/divinylbenzene. Solid phase oligomer synthesis is in principle based on the well-known Merrifield synthesis and the Carruthers-Köster phosphoramidite method.

Another aspect of the invention is the use of a compound according to the invention for interacting, by way of a physical interaction, with a target molecule. Likewise, another aspect of the invention is the use of a compound obtainable by a process according to the invention for interacting with a target molecule.

According to the invention this interaction occurs in a solution, preferably in an aqueous solution. The preferred target molecule according to the invention is a biomolecule. However, the interaction of a compound according to the invention and a target molecule invention is by no means limited to biomolecules. Other molecules such as synthetic compounds suitable for being subjected to chromatographic purification are also preferred targets.

One embodiment of the present invention is a library of binding moieties is a combinatorial library or portion thereof. A combinatorial chemical library is a collection of compounds generated by chemical synthesis, by combining a number of chemical "building blocks" in all possible combinations. According to the invention, a building block is understood as being a monomer (a structure depicted in the brackets of Formula 1) in a compound according to Formula 1. A linear combinatorial chemical library is preferably formed by combining a set of monomers in every possible way for a given length of the oligomer (the length being denoted by n in Formula 1). As an example, if the number of building blocks is n=5 and the construct is composed of five members, the number of possible linear combinations is of $5^5$ or 3,125 members. In this case the building blocks (A, B, C, D and E) are assembled linearly such as: A-A-A-A-A; A-A-A-A-B; A-A-A-A-C; A-A-A-B-A; A-A-A-B-B; A-A-A-B-C; . . . A-A-B-A-A; A-A-B-A-B; A-A-B-A-C; . . . ; E-E-E-E-C; E-E-E-E-D; E-E-E-E-E.

Millions of chemical compounds can be synthesized through such combinatorial mixing of chemical building blocks. For oligomers according to Formula 1, the length is preferably limited to 10, 8, 6, 5, 4 or 3 monomers.

Combinatorial libraries may be complete or incomplete. Complete combinatorial libraries are those libraries containing a representative of every possible permutation of monomers for a given oligomer length and composition. Incomplete libraries are those libraries lacking one or more possible permutation of monomers for a given oligomer length.

Combinatorial and synthetic chemistry techniques well-known in the art can generate libraries containing millions of members (Lam, K. S., et al., Nature 354 (1991) 82-84 and WO 92/100091). Owing to the advantages of controlled stereocenters according to the invention, each different structure in the library is not only unique but also reproducible in terms of three-dimensional conformation. Each member of such a library potentially possesses the capacity to bind to a different target molecule.

Members of a combinatorial library can be synthesized on or coupled to a solid support, such as a bead, with each bead essentially having millions of copies of a library member on its surface. However, even more preferred, different library members are synthesized on a solid phase in the form of an array of spots, whereby each spots contains replicates of the same member. Arrays with specified members can be used with great advantage to identify members suited as specifiers for one or more particular target biomolecules.

For clarification, a chemical compound microarray is a collection of organic chemical compounds spotted on predetermined locations of a solid surface, such as glass and plastic. There are several different forms of chemical compound microarrays based on the fabrication method. A first form is to covalently immobilize the organic compounds on the solid surface with a linker moiety. A second form is to spot and dry organic compounds on the solid surface without immobilization. A third form is to spot organic compounds in a homogenous solution without immobilization and drying effect. Further forms are possible. In addition, the solid phase may be a flat surface or may comprise a plurality of wells in which the chemical compound can be located.

The above equally applies to microarrays of compounds which are biomolecules. Such arrays are preferred for assaying interaction of a compound according to the invention and a biomolecule.

Figure 6:
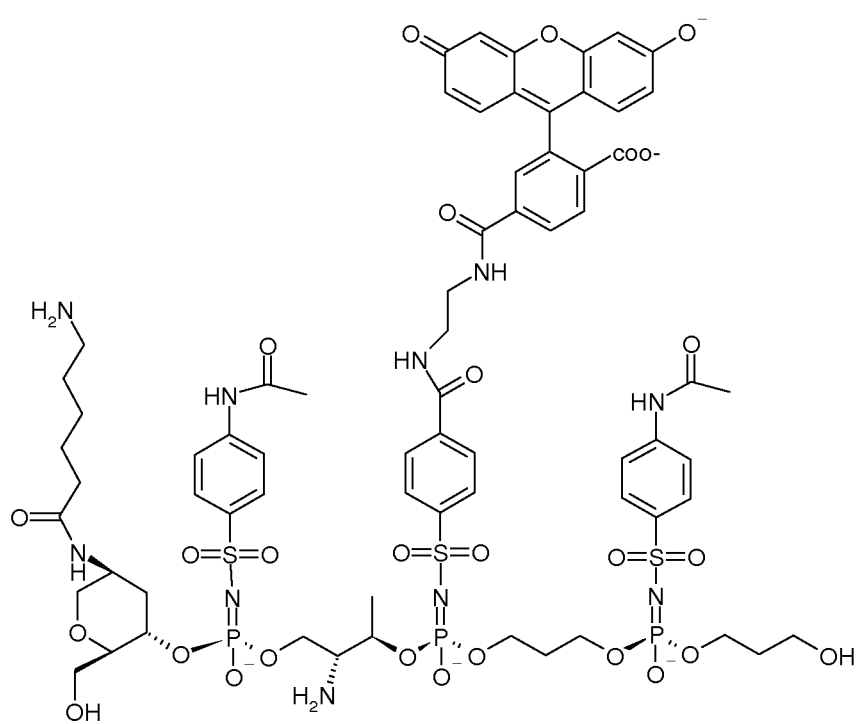
FIG. 6: Oligophosphoramidate according to Formula 1, obtained by the synthesis of Example 4

An example for an oligomer composed of 3 monomers is shown in FIG. 6.

As shown above, the compounds of the invention can easily be synthesized in a great variety. Thus, compounds can be synthesized which are capable of interacting with a target molecule. To this end, a combinatorial library of separately synthesized compounds according to the invention is contacted with a target molecule and interaction is assayed, thereby detecting interaction of one or more compounds and the target molecule.

Alternatively, a library of biomolecules is probed with a compound of the invention. Thus, upon building up an oligomer according to Formula 1 the oligomer is separated from the solid phase. Preferably, the oligomer comprises a detectable moiety, e.g. biotin or a fluorescent dye. The library of biomolecules is preferably in the form of an array with replicates of each member being present in distinct spots with known location in the array. The array is then incubated with a solution of the oligomer under different conditions (solvent, solutes, pH, buffer substances, concentration of oligomer, total concentration of solutes in solution, temperature, incubation time, etc.) thereby allowing interaction of the compound and one or more biomolecules. Unbound compound is subsequently washed away under different conditions of stringency (e.g. variant concentration of solutes, pH, competitor substances) and bound compound is detected by way of detecting the detectable moiety. In the very convenient embodiment of a fluorescent dye, detection can be done by illuminating the array with e.g. UV light and detecting array spots emitting fluorescent light. More generally, light with a suitable excitation wave length is used to stimulate light emission by the fluorescent dye. By these means a specifier for a target molecule (biomolecules preferred) can be established and characterized. In a preferred embodiment the target molecule is selected from the group consisting of a peptide, a protein, a polysaccharide, a lipid, and a complex comprising one or more of these compounds.

The nature of the interaction between the specifier and the target can be manifold. Thus, as a result of the interaction the compound of the invention may physically interact with the target molecule. Preferably, the interaction between the target molecule and the compound of the invention is specific.

Following detection, the compound capable of interacting with the target molecule may optionally undergo further refinement, preferably by exchanging one or more substituents such as R1 and R2 or by introducing modifications in T1 and T2, according to the invention. Thus, refinement can be used to fine-tune the interaction between the compound according to the invention and the target molecule. This way an improved specifier can be provided.

A solid phase be coupled to a particular library member capable of acting as a specifier for a particular target molecule. This way material for use as a stationary phase for interaction chromatography is provided. A preferred embodiment thereof is affinity chromatography. From a complex mixture containing the target molecule the target can thus be purified, whereby the mixture as well as the target molecule need to be amenable to chromatography. To this end, preparation of a sample containing the complex mixture may be necessary, e.g. for solubilizing constituents of the sample including the target molecule.

Further aspects of the present invention are presented in the following items.

1. A chemical compound according to Formula 1 according to the invention and according to the description above,

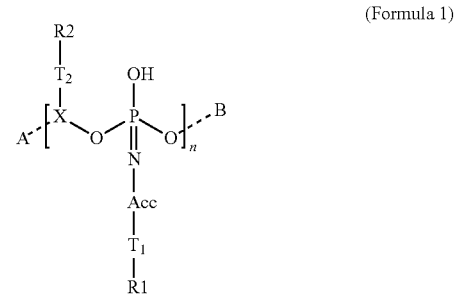

(Formula 1)

in which the monomer in the brackets is repeated n times;

in which n is an integer denoting the number of monomers, and n is equal to or higher than 2; and whereby the compound of Formula 1 is a defined stereoisomer.

2. The compound according to item 1, characterized in that in a monomer the $sp^3$ C atom of X which is connected to T2 or R2 is a stereocenter.

3. The compound according to any of the items 1 and 2, characterized in that in a monomer the P atom of the phosphoramidate moiety is a stereocenter.

4. The compound according to any of the items 2 and 3, characterized in that for each monomer the stereoconformation of each stereocenter is selected independently from the respective stereocenters of the other monomers.

5. The compound according to item 1, characterized in that X does not contain a stereocenter.

6. The compound according to item 5, characterized in that X is a —$(CH_2)_3$— or a bis-p-methylenephenylene residue or a 3,5-bismethylenephenylene residue which is substituted with T2-R2 in the −1 position.

7. The compound according to item 2, characterized in that a monomer comprises a structure according to Formula 5.

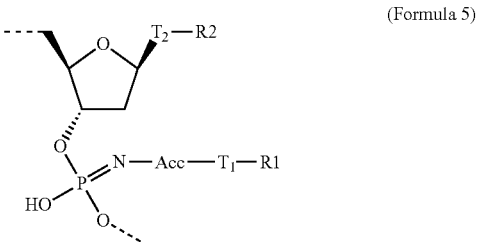

(Formula 5)

8. The compound according to item 2, characterized in that a monomer comprises a structure according to Formula 6.

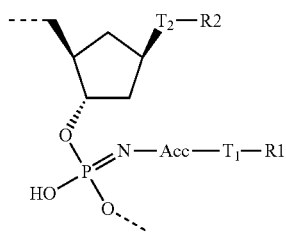
(Formula 6)

9. The compound according to item 2, characterized in that a monomer comprises a structure according to Formula 7.

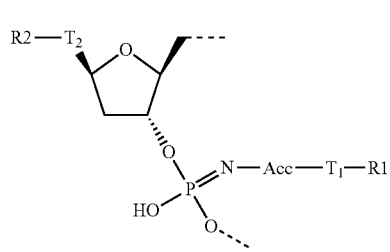
(Formula 7)

10. The compound according to item 2, characterized in that a monomer comprises a structure according to Formula 8.

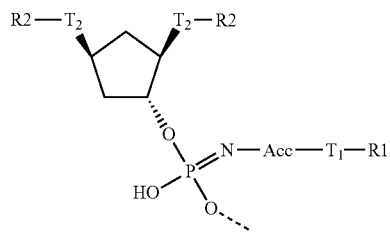
(Formula 8)

11. The compound according to item 2, characterized in that a monomer comprises a structure according to Formula 9.

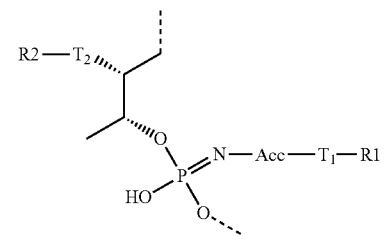
(Formula 9)

12. The compound according to item 2, characterized in that a monomer comprises a structure according to Formula 10.

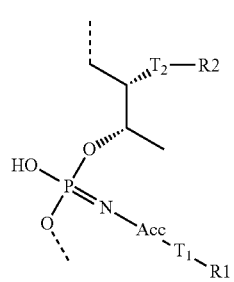
(Formula 10)

13. The compound according to item 2, characterized in that a monomer comprises a structure according to Formula 11.

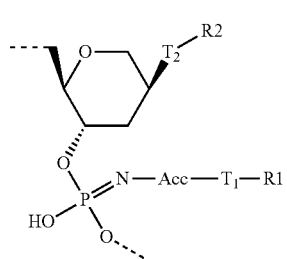
(Formula 11)

14. A compound according to any of the items 7 to 13, characterized in that in a monomer T2 comprises a —C=O—NH— group or a —NH—C=O— group attached to the stereocenter of X.

15. The compound according to item 1, characterized in that n is between 2 and 10.

16. The compound according to item 15, characterized in that n is an integer selected from the group consisting of 2, 3, 4, 5, 6, 8, and 10.

17. The compound according to item 15, characterized in that n=3.

18. The compound according to item 15, characterized in that n=4.

19. Process for producing a compound according to item 1, according to the invention and according to the description above and the disclosure in the Examples.

20. The process according to item 19, characterized in that the solid phase of step (a) is controlled pore glass functionalized with succinyl residues, whereby each succinyl residue is attached to a trifunctional linker.

21. The process according to item 20, characterized in that the trifunctional linker is a branched C3-C10 alkyl residue substituted with two —OH groups of which a first —OH residue is covalently linked with succinate, and the second —OH residue is protected with a PG1 protection group, and said branched C3-C10 alkyl residue is substituted with a third moiety selected from the group consisting of —CH=CH₂, —C≡CH, a detectable moiety, and a protected (if necessary) reactive functional group selected from group consisting of —SH, —NH₂, —O—NH₂, —NH—NH₂, —C(=O)H, —COOH, and —OH.

22. The process according to according to any of the items 19-21, characterized in that following step (p) and before the execution of step (q) an additional step (p') is performed, the step comprising the substeps of reacting the free hydroxyl group with a beta-cyanoethyl-diisopropyl-linear or branched C3-C10 alkyl phosphoramidite wherein said C3-C10 alkyl residue is substituted with a moiety selected from the group consisting of —CH=CH$_2$, —C≡CH, a detectable moiety, and a protected reactive functional group selected from the group consisting of —SH, —NH$_2$, —O—NH$_2$, —NH—NH$_2$, —C(=O)H, —COOH, and —OH.

23. The process according item 19, characterized in that in step (o) an acid-labile protective group PG1 is reacted with trichloracetic acid or dichloracetic acid.

24. The process according to item 19, characterized in that the compound according to Formula 2 in step (b) or step (i) comprises a compound according to Formula 12.

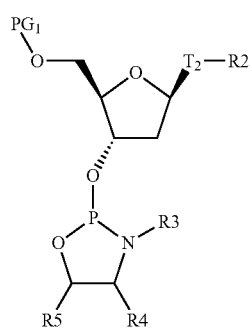

(Formula 12)

25. The process according to item 19, characterized in that the compound according to Formula 2 in step (b) or step (i) comprises a compound according to Formula 13.

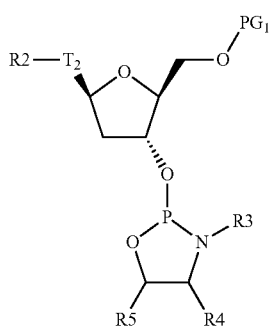

(Formula 13)

26. The process according to item 19, characterized in that the compound according to Formula 2 in step (b) or step (i) comprises a compound according to Formula 14.

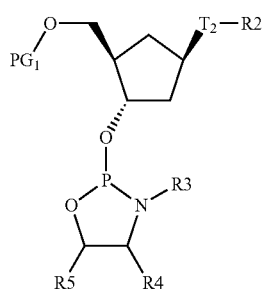

(Formula 14)

27. The process according to item 19, characterized in that the compound according to Formula 2 in step (b) or step (i) comprises a compound according to Formula 15.

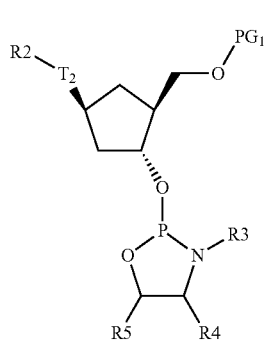

(Formula 15)

28. The process according to item 19, characterized in that the compound according to Formula 2 in step (b) or step (i) comprises a compound according to Formula 16.

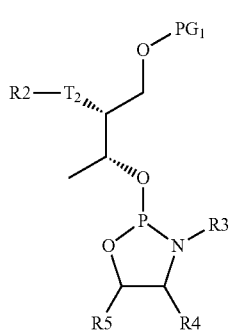

(Formula 16)

29. The process according to item 19, characterized in that the compound according to Formula 2 in step (b) or step (i) comprises a compound according to Formula 17.

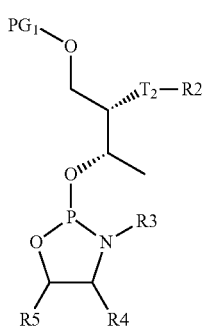

(Formula 17)

30. The process according to item 19, characterized in that the compound according to Formula 2 in step (b) or step (i) comprises a compound according to Formula 18.

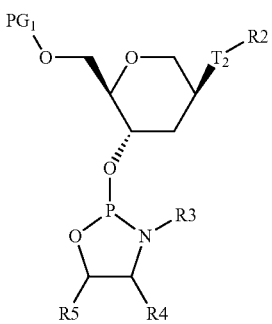

(Formula 18)

31. The process according to item 19, characterized in that the compound according to Formula 2 in step (b) or step (i) comprises a compound according to Formula 19.

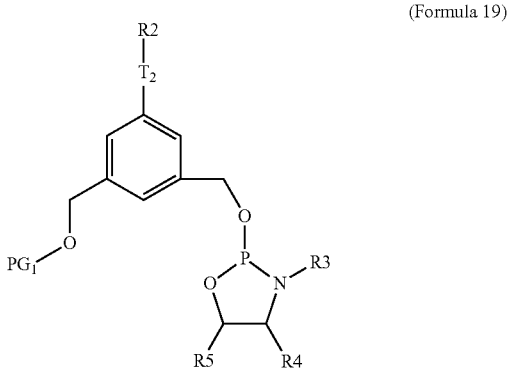

(Formula 19)

32. The process according to item 19, characterized in that in a monomer R3 and R4 are —(CH$_2$)$_3$— and R5=H, whereby the oxazaphospholidine in which the stereogenic carbon atom is located is either in the R or S conformation, according to Formula 20 and Formula 21, respectively.

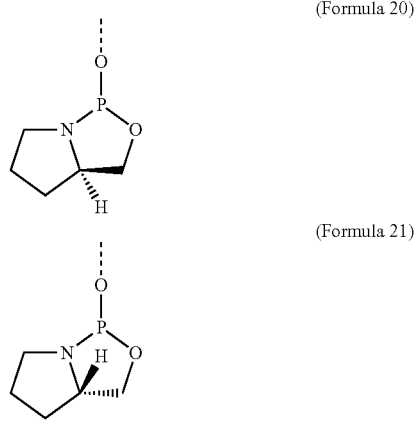

(Formula 20)

(Formula 21)

33. A compound according to item 1, obtainable by the process according to any of the items 19 to 32.
34. A conjugate of (i) a compound according to any of the items 1-18 and according to item 33 with (ii) a biomolecule selected from the group consisting of a peptide, a protein, an oligonucleotide, a lipid, and a carbohydrate.
35. The use of a compound according to any of the items 1 to 18 and according to item 33 for interacting, by way of a physical interaction, with a target molecule.
36. The use according to item 35, characterized in that the interaction is selected from the group consisting of ionic interaction, hydrogen bonding, van-der-Waals type of interaction and formation of a complex.
37. The use according to any of the items 35 and 36, characterized in that the interaction occurs in solution.
38. The use according to item 37, characterized in that the solution is an aqueous solution.
39. The use according to any of the items 35 to 38, characterized in that the target molecule is a biomolecule.
40. The use according to item 39, characterized in that the target molecule is selected from the group consisting of a peptide, a protein, a polysaccharide, and a lipid.
41. The use according to any of the items 39 and 40, characterized in that the interaction is specific for the target.
42. An array comprising a solid phase and a plurality of compounds according to item 1, whereby the compounds are covalently attached to the solid phase.
43. The array according to item 42, characterized in that said plurality of compounds comprises members with different compositions of monomers.
44. A method of assessing non-covalent binding comprising the steps of contacting a compound according to item 1 with a protein, and detecting the protein with the bound compound.
45. The method according to item 44, characterized in that the protein is immobilized on a solid phase.
46. The method according to claim 44, characterized in that the compound according to claim 1 is immobilized on a solid phase.

The following examples and figures are provided to aid the understanding of the present invention, the true scope of which is set forth in the appended claims. It is understood that modifications can be made in the procedures set forth without departing from the spirit of the invention.

EXAMPLES

1. Compounds According to Formula 2, and Precursor Compounds 1.1 Stereoisomeric Phosphitylation Reagents 1-1 and 1-2

1.1.1

1-chlorotetrahydro-,(1S,3aS)—H, 3H-Pyrrolo[1,2-c][1,3,2]oxazaphosphole

In order to introduce stereoselectivity, L-prolinol was reacted with PCl3 according to Iyer, R. P., et al., Tetrahedron Letters 39 (1998) 2491-2494 and Tsarev, V. N., et al., Eur. J. Org. Chem. 10 (2005) 2097-2105, and the resulting phosphitylation reagent was destilled under reduced pressure. By way of this scheme phosphitylation reagent 1-1 was obtained.

At −40° C. a solution of 30 ml (304 mmol) 1-Prolinol in 100 ml dry toluene was dropped within 25 min under vigorous stiffing and under argon to a solution of 26.5 ml PCl3 (304 mmol) and 100.3 ml (912 mmol) N-methyl morpholin in 400 ml dry toluene. A yellow suspension was formed after stiffing for on hour at −40° C. the mixture was allowed to war up to room temperature and was stirred for additional 90 min. The mixture was stored over night at room temperature. The precipitate was removed by filtration under argon. The filtrate was concentrated using a rotary evaporator and the reminder was destilled under high vacuum. Fractions were monitored by 31 P NMR spectroscopy. Yield of combined fractions: 13.03 g Yield: 13.03 g, colourless oil; $^{31}$P-NMR (CDCl$_3$)=172.6 ppm 1.1.2

1-chlorotetrahydro-(1R,3aS)-1H,3H-Pyrrolo[1,2-c][1,3,2]oxazaphosphole,

In order to introduce stereoselectivity, D-prolinol was reacted with PCl3 according to Iyer, R. P., et al., Tetrahedron Letters 39 (1998) 2491-2494 and Tsarev, V. N., et al., Eur. J. Org. Chem. 10 (2005) 2097-2105, and the resulting phosphitylation reagent was destilled under reduced pressure. By way of this scheme phosphitylation reagent 1-2 was obtained.

1.2 Stereoisomeric Phosphoramidites (Compounds According to Formula 2, without Stereocenter in the Spacer Part X)

1.2.1

O1-(DMT)propane-1,3-diol (commercially available from Berry and Assoc. Dexter Mich. USA) was reacted with the phosphitylation reagent 1-chlorotetrahydro-(1S,3aS)-1H, 3H-Pyrrolo[1,2-c][1,3,2]oxazaphosphole (phosphitylation reagent 1-1) in the presence of N Ethyl-diisopropylamine according to standard procedures. The phosphoramidite was purified by column chromatography on silica gel using hexane/acetone gradient as eluent.

To a solution of 0, 4 g (1.1 mmol) O1-(DMT)propane-1,3-diol in 10 ml dry THF 0.54 ml (3.2 mmol) N Ethyl diisopropylamin was added. The mixture was cooled to 0-5° C. and under stirring and under argon a solution of 0.232 g (1.4 mmol) 1-chlorotetrahydro-(1S,3aS)-1H,3H-Pyrrolo[1,2-c][1,3,2]oxazaphosphole in 5 ml dry THF was added slowly. The reaction was monitored by TLC (hexane. Acetone+0.5% Triethylamine) 5:1. After stirring at 0-5° C. for 30 min the ice bath was removed and the mixture was stirred for additionally 30 min, The product was purified by column chromatography on silica gel using hexane/acetone gradient as eluent. Yield: 0.4 g $^{31}$P-NMR (Bruker 400 MHz):

Yield: 0.6 g, clear yellow oil; $^{31}$P-NMR (CDCl$_3$)=139.0 ppm

1.2.2

O1-(DMT)propane-1,3-diol (commercially available from Berry and Assoc. Dexter Mich. USA) was reacted with the phosphorylating reagent 1-chlorotetrahydro-(1R,3aS)-1H, 3H-Pyrrolo[1,2-c][1,3,2]oxazaphosphole (phosphitylation reagent 1-2) in the presence of N,Ethyl-diisopropylamine according to standard procedures. The phosphoramidite was purified by column chromatography on silica gel using hexane/acetone gradient as eluent.

1.3 Precursor Alcohols with Stereocenters 2-amino-1,5-anhydro-6-O-[bis(4-methoxyphenyl)phenylmethyl]-2,3-dideoxy-D-ribo-hexitol was reacted with different substituted carboxylic acids according to EP 1431298A1. In cases where the carboxylic acid contained a reactive group this group was protected.

1.3.1

An exemplary synthesis was the preparation of 6-O-(4,4'-Dimethoxytrityl)-2[N-(9-fluorenylmethoxycarbonyl)-6-aminohexanoylamido]-1,5-anhydro-2,3-dideoxy-D-mannitol. The reaction with FMOC aminocaproic acid resulted in the formation of 1,5-anhydro-6-O-[bis(4-methoxyphenyl) phenylmethyl]-2,3-dideoxy-2-[[6-[[(9H-fluoren-9-yl-methoxy)carbonyl]amino]-1-oxohexyl]amino]-D-ribo-hexitol (for further details see EP 1431298A1, Example 16).

1.3.2

A mixture of 150 mg (0.33 mmol) 2-amino-1,5-anhydro-6-O-[bis(4-methoxyphenyl)phenylmethyl]-2,3-dideoxy-D-ribo-Hexitol in 20 ml methylenehloride was stirred overnight with 176 mg (0.36 mmol) Fmoc Phenylalanin NHS ester (Bachem) at room temperature under argon. The solvent was evaporated by using a rotary evaporator and the reminder was purified by column chromatography on silica with acetic acid ethylester/hexane (2:1) as eluent.

1.4 Stereoisomeric Phosphoramidites (Compounds According to Formula 2, with Stereocenter in the Spacer Part X)

1.4.1

The hexitol derivative according to 1.3.1 was transformed in the phoshophoramidite analogous to the reactions described above under 1.2. with the phosphitylation reagent according to either 1-1 or 1-2, and purified.

1.4.2

The hexitol derivative according to 1.3.2 was transformed in the phoshophoramidite analogous to the reactions described above under 1.2. with the phosphitylation reagent according to either 1-1 or 1-2, and purified.

1.4.3

To a solution of 1.5 g (2.75 mmol) 5'O (DMT) Thymidine in 20 ml dry THF 1.41 ml (8.26 mmol) N Ethyl diisopropylamin was added. The mixture was cooled to 0-5° C. and under stirring and under argon a solution of 1.0 g (6.06 mmol) 1-chlorotetrahydro-(1S,3aS)-1H,3H-Pyrrolo[1,2-c][1,3,2] oxazaphosphole in 10 ml dry CHCl$_3$ was added slowly. The reaction was monitored by TLC (toluene aceticacid ethylester methanol+0.5% Triethylamine) 4:4:1. After stirring at 0-5° C. for 90 min the ice bath was removed and the mixture was stirred for additionally 150 min. the reaction was quenched with 0.5 ml isopropanol. The solvents were removed by using a rotary evaporator. The reminder was dissolved in dry THF and precipitated by hexane. $^{31}$P-NMR (Bruker 400 MHz):

Yield: 0.78 g, $^{31}$P-NMR (CD$_3$CN)=139.6 ppm

1.5 Precursor Alcohols with Stereocenters

1.5.1

The procedure described in Beres, J., et al., J. Med. Chem. 33(5) (1990) 1353-1360 was used to synthesize a precursor alcohol based on carbadeoxyribose.

1.5.2

The procedure described in WO 92/02532 and Valis, L., and Wagenknecht, H.-A., Synlett 13 (2007) 2111-2115 was used to synthesize a precursor alcohol based on threoninol.

1.5.3

Precursor alcohols based on 2,5-anhydro-3-deoxy-,D-Gluconic acid were prepared according to Kawakami, J., et al., Chemistry Letters 33(12) (2004) 1554-1555.

1.6 Stereoisomeric Phosphoramidites (Compounds According to Formula 2, with Stereocenter in the Spacer Part X)

1.6.1

The compound according to 1.5.1 was transformed in the phoshophoramidite analogous to the reactions described above under 1.2. with the phosphitylation reagent according to either 1-1 or 1-2, and purified.

1.6.2

The compound according to 1.5.2 was transformed in the phoshophoramidite analogous to the reactions described above under 1.2. with the phosphitylation reagent according to either 1-1 or 1-2, and purified.

1.6.3

The compound according to 1.5.3 was transformed in the phoshophoramidite analogous to the reactions described above under 1.2. with the phosphitylation reagent according to either 1-1 or 1-2, and purified.

2. Compounds According to Formula 3, and Precursors Thereof

2.1 p-Azidosulfonyl Benzene Carboxylic Acid Chloride (Precursor)

Under Argon at 0° C. and while stiffing, 0.7 ml oxalylchloride were added dropwise to a suspension of 908 mg (4 mmol) 4-carboxybenzene sulfonyl azide (Aldrich). The mixture was allowed to warm to room temperature. Then, 10 µl DMF (dimethylformamide) were added. After stirring for 1 h at room temp. a clear solution was formed. The solvent was removed using a rotary evaporator.

In subsequent synthesis steps (see below) the resulting carboxylic acid chloride was reacted with amines to form compounds according Formula 3.

2.2 Compound According to Formula 3

To a solution of 50 mg (0.08 mmol) of Lissamine rhodamine B ethylenediamine (Molecular Probes, Eugene, Oreg.) and 34 µl triethylamin in 5 ml Chloroform a solution of 22 mg (0.09 mmol) of p-azidosulfonyl benzene carboxylic acid chloride dissolved in 1 ml Chloroform was added. After stirring for 1 h at room temperature 50 ml Toluol was added and the solvents were removed by using a rotary evaporator. The reminder was purified by using column chromatography on silica gel. Eluent Toluene/Aceticacidethylester/methanol (3:1:1).

2.3 Compound According to Formula 3

Alternatively p-azidosulfonyl benzene carboxylic acid chloride was transformed in an amine which could be reacted with carboxylic acid derivatives.

For this purpose, a solution of 262 mg (1 mmol) of the p-azidosulfonyl benzene carboxylic acid chloride in 5 ml Methylenehloride was dropped to a solution of 1.1 mmol N—BOC ethylendiamin and 139 µl Triethylamin in 20 ml Methlyenchloride. After 12 h stirring at room temperature the mixture was extracted with water and the separated organic phase was dried over sodium sulfate. After filtration the solvent was removed using a rotary evaporator and the reminder was used without further purification.

The Boc group was removed by adding 1 ml 37% HCl and stiffing for 30 min. The solvent was evaporated and than water was added. The water was removed again by using a rotary evaporator. Subsequently, a series of adding different solvents with intermediate evaporation was performed: Firstly twice with acetone, then once with chloroform, then with acetonitrile. The reminder N(p azido sulfonyl benzene carboxy)-ethylendiamin hydrochloride was used without further purification for reaction with activated carboxylic acids.

30 mg (0, 1. mmol) N(p azido sulfonyl benzene carboxy) ethylendiamin hydrochloride were given to 10 ml methylenchlorid. After adding of 20 µl triethylamin 70 mg (0.11 mmol) bispivaloyl-6 carboxy-fluorescein N hydroxy succinimid ester was added. The mixture was stirred for 1 h at room temperature under argon. 10 ml Toluene were added and the solvents removed by using a rotary evaporator. The reminder was purified by using column chromatography on silica gel. Eluent Toluene/Aceticacidethylester/methanol (3:1:1).

3. Synthesis of Phosphoramidates

3.1 Oligophosphoramidate (n=1)

The oligophosphoramidate is synthesized in 10 µmol scale on an ABI 394 synthesizer using the phosphoramidites according to 1.2.1 or 1.2.2. As solid support a 1-O-Dimethoxytrityl-propyl-disulfide, 1'-succinyl-1caa-CPG (Glenresearch Id. No. 20-2933) was used. All chemicals for the standard protocol were from Proligo or ABI. The synthesis followed the standard protocol except the oxidation. Oxidation was performed with 0.1 M 4-Acetamidobenzenesulfonyl azide (Fluka) in acetonitrile 2 times for 30 min. The product was detritylated, and cleaved form the solid support and deprotected with 30% aqueous $NH_3$ (4 h 55° C.).

3.2 Oligophosphoramidate (n=1)

The oligophosphoramidate is synthesized in 1 µmol scale on an ABI 394 synthesizer using the phosphoramidites according to 1.2.1. As solid support a-(1-Dimethoxytrityloxy-propanediol-3-succinoyl)-long chain alkylamino-CPG (Glenresearch Id. No. 20-2913) was used. All chemicals for the standard protocol were from Proligo or ABI. The synthesis followed the standard protocol except the oxidation. Oxidation was performed with 0.1 M 4-Acetamidobenzenesulfonyl azide (Fluka) in acetonitrile 2 times for 30 min. The DMTrON-product was cleaved form the solid support and deprotected with 30% aqueous $NH_3$ (4 h 55° C.).

Mass spec. 712 found

3.3 Oligophosphoramidate (n=1)

The oligophosphoramidate is synthesized in 4 µmol scale on an ABI 394 synthesizer using the dT phosphoramidites according to 1.4.3. As solid support a-(1-Dimethoxytrityloxy-propanediol-3-succinoyl)-long chain alkylamino-CPG (Glenresearch Id. No. 20-2913) was used. All chemicals for the standard protocol were from Proligo or ABI. The synthesis followed the standard protocol except the oxidation. Oxidation was performed with 0.1 M 4-Acetamidobenzenesulfonyl azide (Fluka) in acetonitrile 2 times for 30 min. The DMTrON-product was cleaved form the solid support and deprotected with 30% aqueous $NH_3$ (4 h 55° C.).

31P-NMR (DMSO)=−3.7 ppm (single peak refers to a single diastereoisomer)

Mass. spec. 878 found

4. Synthesis of Oligophosphoramidates (N=3)

4.1

The oligophosphoramidate was synthesized in 1 µmol scale on an ABI 394 synthesizer. As solid support was used a (1-Dimethoxytrityloxy-propanediol-3-succinoyl)-long chain alkylamino-CPG (Glenresearch Id. No. 20-2913). All chemicals for the standard protocol were from Proligo or ABI. The synthesis followed the standard protocol except for the oxidation. First coupling was done with a phosphoramidite according to 1.2.1 followed by capping with acetanhydride and then by oxidation with 0.1 M-Acetamidobenzenesulfonyl azide (Fluka) in acetonitrile 2 times for 30 min; after capping and detritylation the second coupling was done with a Fmoc-L-threoninol dimethoxytrityl phosphoramidite according to 1.6.2 followed by capping and then oxidation with 0.1 M N-(bis pivaloyl-6-carboxy-fluorescein) N'(p-sulfonylazido carboxy phenyl)ethylendiamin according to 2.3 in acetonitrile 2 times for 30 min. The last coupling was done with a phosphoramidite according to 1.4.1 followed by capping and then oxidation with 0.1 M-Acetamidobenzenesulfonyl azide (Fluka) in acetonitrile 2 times for 30 min., The product was detritylated, and cleaved form the solid support and deprotected with 30% aqueous $NH_3$ (4 h 55° C.). Purification was performed by reversed phase chromatography on a RP 18 column with an 0.1 M Triethylammoniumacetate in water to a 0.1 M Triethylammonium acetate in water/acetonitril 1:1 gradient.

The product is shown on FIG. 6.

4.2

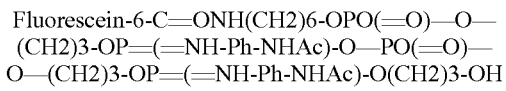

The oligophosphoramidate was synthesized in 1 µmol scale on an ABI 394 synthesizer. As solid support was used a (1-Dimethoxytrityloxy-propanediol-3-succinoyl)-long chain alkylamino-CPG (Glenresearch Id. No. 20-2913). All chemicals for the standard protocol were from Proligo or ABI. The synthesis followed the standard protocol except for the oxidation. First coupling was done with a phosphoramidite according to 1.2.1 followed by capping with acetanhydride and then by oxidation with 0.1 M-Acetamidobenzenesulfonyl azide (Fluka) in acetonitrile 2 times for 30 min; after capping and detritylation the second coupling was done with a phosphoramidite according to 1.2.1 followed by capping and then oxidation with 0.1 M-Acetamidobenzenesulfonyl azide (Fluka) in acetonitrile 2 times for 30 min; The last coupling was done with 5'-Fluorescein Phosphoramidite (Glen Res 10-5901) followed by capping and standard oxidation with 0.02M I2 in THF/Pyridine/H2O for 3 min. The product was detritylated, and cleaved form the solid support and deprotected with 30% aqueous $NH_3$ (4 h 55° C.). Purification was performed by reversed phase chromatography on a RP 18 column with an 0.1 M Triethylammoniumacetate in water to a 0.1 M Triethylammonium acetate in water/acetonitril 1:1 gradient. Mass spec. 1224 found 5. Specific Interaction with Proteins on a Protein Chip In the experimental procedure the UNIchip® AV-400 (Prot@gen AG, Dortmund, Germany) was used. The chip contains 400 selected and purified human proteins on a nitrocellulose-coated glass slide. In a first step, the chip was incubated with BSA-containing blocking buffer, following the instructions of the manufacturer. The oligomer (oligophosphoramidate obtained in Example 4) was used in different concentrations of between 10 nM and 10 µM. The oligophosphoramidate was dissolved in a buffer containing 2% [w/v] BSA in 10 mM TrisHCl pH 7.5, 150 mM NaCl in water. The protein biochips were incubated between 12 h and 24 h, and a humidified atmosphere and at a temperature of 4° C. A further series of experiments was performed overnight at room temperature.

Replicate experiments were performed under identical conditions, however without using BSA.

After incubation, the chips were washed with 20 mM TrisHCl pH 7.5, 500 mM NaCl, 0.1% (v/v) TWEEN, three times according to the instructions of the manufacturer. A final rinse with distilled water was performed optionally.

The slides were dried by first placing each slide in a 50 ml tube. The tubes were centrifuged at 800×g for 3-5 min at room temperature.

The slides were inspected using an Axon GenePix 4000B microarray scanner (Molecular Devices, Sunnyvale, Calif., USA).

What is claimed is:

1. A process for producing a compound comprising the steps of:
    (a) providing a solid support to which is attached a hydroxyalkyl group via a cleavable or non-cleavable linker,
    (b) supplying a first compound according to Formula 2:

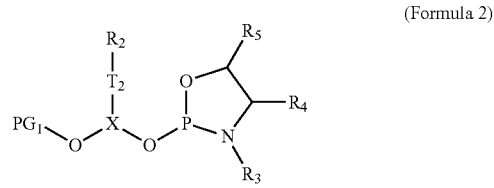

(Formula 2)

wherein X is a spacer consisting of 2-16 atoms, whereby the spacer is selected from the group consisting of:
    branched or linear alkyl,
    linear C4-C14 heteroalkyl with one N atom,
    branched or linear C4-C14 alkenyl,
    branched or linear C4-C14 alkinyl,
    bis-(C1-C3)-alkyl-(C6-C10)-aryl,
    bis-(C1-C3)-alky-heteroaryl, with 5-6 membered heteroaryl with 1-3 heteroatoms selected from N, O and S,
    5-10 membered cycloalkyl,
    5-10 membered heteroalkyl structure with 2 heteroatoms, whereby each heteroatom is independently selected from the group consisting of N, O, and S,
    5-10 membered cyclo-heteroalkyl structure with 1-5 heteroatoms, whereby each heteroatom is independently selected from the group consisting of N, O, and S;
in which the atom or atoms of X which are connected to phosphoramidate are $sp^3$ C atoms;
in which R2 in the monomer is a moiety selected from the group consisting of
    a hydrogen atom,
a core moiety selected from the group consisting of:
    a linear or branched C1-C6 alkyl group,
    a linear or branched C2-C6 alkenyl group,
    a linear or branched C2-C6 alkinyl group,
    a 5-10 membered cycloalkyl group,
    a 6-10 membered aryl group,
    a 5-10 membered heterocyclic group with 1-5 heteroatoms, whereby each heteroatom is independently selected from N, O, and S;

a substituent attached to the core moiety, whereby the substituent is selected from the group consisting of:
a hydrogen atom,
a halogen atom,
a protected carboxyl group,
a protected formyl group,
a C1-C6 acyl group,
a C6-C10 aroyl group,
a protected hydroxyl group,
a C1-C6 acylamino group,
a protected amino group,
a carboxamido group,
a protected mercapto group,
a cyano group,
a nitro group,
a C1-C6 alkoxy group,
a C1-C6 alkoxycarbonyl group,
a C6-C10 aryloxy group,
a C6-C10 aryloxycarbonyl group,
a protected sulfhydryl group,
a C6-C10 aryl- or C1-C6 alkyl-sulfonyl group,
a protected phosphatyl group,
a guanidyl group,
a primary or secondary carboxyamido group,
a detectable moiety,
a C6-C10 aryl group,
a C2-C6 alkenyl group,
a C2-C6 alkinyl group,
a 5-10 membered heteroaryl group;
in which T2 in the monomer is a tether consisting of a linear, branched or cyclic organic moiety comprising 1-30 C— atoms and 0-5 heteroatoms selected from N, O, and S, and 1-3 subunits selected from a carboxy moiety, an amide moiety and a urea moiety, whereby the internal heteroatoms with the exception of a disulfide bond are separated from each other by a minimum of two carbon atoms;
in which
R3 is selected from a first group of substituents consisting of H, C1-C3-alkyl, or
R3 is selected from a second group of substituents consisting of acetyl, monofluor-acetyl, and difluor-acetyl;
in which R4 is selected from the group consisting of H, C1-C3 alkyl, and C6-C10 aryl;
in which R3 and R4 are optionally covalently connected to form a —(CH$_2$)$_n$-bridge with n=3 or n=4;
in which R5 is selected from the group consisting of H, C1-C3 alkyl, and C6-C10 aryl; and
in which PG 1 is either a photo-cleavable linker selected from the group consisting of NVOC and NPPOC, or PG 1 is an acid-cleavable linker selected from the group consisting of monomethoxytrityl, dimethoxytrityl, trimethoxytrityl, 9-phenylxanthine-9-yl (Pixyl), and 9-(p-methoxyphenyl)xanthine-9-yl (MOX);
(c) in case that R3 consists of the first group of substituents or in case R3 is covalently linked to R4 performing the step of activating the compound of step (b) with an activator selected from
IH-tetrazole, dicyano-imidazole,
N-phenylimidazolium triflate, N-methylbenzimidazolium triflate, and
N-(cyanomethyl)pyrrolidinium triflate,
or in case R3 consists of the second group of substituents performing the step of activating the compound of step (b) with N,N,N',N'-tetramethylguanidine thereby providing an activated compound;

(d) reacting the activated compound of step (c) with the hydroxyl group of step (a), thereby forming a phosphate triester,
whereby in the case of R3 being selected from the first group a beta-amino function with R6=H is formed, and
whereby in the case of R3 being selected from the second group an acylated beta-amino function is formed;
(e) in case that R3 consists of the first group of substituents, performing the step of capping the beta amino group of step (d) with acetanhydride thereby introducing R6=acetyl, and proceeding with step (f),
otherwise directly proceeding with step (f);
(f) reacting the capped compound of step (e) or the compound of step (d) with a compound of Formula 3

(Formula 3)

in which R1 is selected independently from R2 and R1 is selected from the group consisting of:
a hydrogen atom,
a halogen atom,
a protected carboxyl group,
a protected formyl group,
a C1-C6 acyl group,
a C6-C10 aroyl group,
a protected hydroxyl group,
a C1-C6 acylamino group,
a protected amino group,
a carboxamido group,
a protected mercapto group,
a cyano group,
a nitro group,
a C1-C6 alkoxy group,
a C1-C6 alkoxycarbonyl group,
a C6-C10 aryloxy group,
a C6-C10 aryloxycarbonyl group,
a protected sulfhydryl group,
a C6-C10 aryl- or C1-C6 alkyl-sulfonyl group,
a protected phosphatyl group,
a guanidyl group,
a primary or secondary carboxyamido group,
a detectable moiety,
a C6-C10 aryl group,
a C2-C6 alkenyl group,
a C2-C6 alkinyl group,
a 5-10 membered heteroaryl group,
in which T1 is a further tether and is selected independently from T2, and T1 is selected from the group consisting of a linear, branched or cyclic organic moiety comprising 1-30 C— atoms and 0-5 heteroatoms selected from N, O, and S, and 1-3 subunits selected from a carboxy moiety, an amide moiety and a urea moiety, whereby the internal heteroatoms with the exception of a disulfide bond are separated from each other by a minimum of two carbon atoms, in which Acc is an electron acceptor selected from the group consisting of:
- a methyl-sulfonyl,
- a C6-C10 aryl-sulfonyl,
- a C5-C6 heteroaryl-sulfonyl with 1 or 2 heteroatoms selected from N, O, and S,
- a C5-C10 cycloalkyl-sulfonyl,
- a 6 membered electron-deficient aromatic ring, and
- heteroaromatic ring with a six-membered heterocycle with at least one alkylated N-atom in ortho- or para-position, said heterocycle being selected from the group consisting of pyridinium, pyrimidinium and chinolinium;

thereby forming a protected and immobilized monomer;

(g) capping the non-reacted free hydroxyl groups of the solid support with acetanhydride or pivaloylanhydride;

(h) alternatively, if PG 1 is a photo-cleavable protective group, the method further includes the step of removing PG 1 by applying UV light to the protected and immobilized monomer, or if PG 1 is an acid-labile protective group, the method further includes the step of removing PG 1 by applying acidic conditions to the protected and immobilized monomer, whereby on the immobilized monomer a new free hydroxyl group is formed;

(i) providing a further compound according to Formula 2, whereby R2, R3, R4, R5, T2, PG1 and X are selected independently from each other and independently from the respective R2, R3, R4, R5, T2, PG 1 and X in each other monomer;

if R3 is selected from the first group of substituents or in if R3 is covalently linked to R4;

(j) performing the step of activating the compound of step (b) with an activator selected from
- IH-tetrazole, dicyano-imidazole,
- N-phenylimidazolium triflate, N-methylbenzimidazolium triflate, and
- N-(cyanomethyl)pyrrolidinium triflate, if R3 is selected from the second group of substituents, the method further includes activating the compound of step (b) with N,N,N',N'-tetramethylguanidine, thereby providing an activated further compound;

(k) reacting the free hydroxyl group formed during step (h) with the activated compound of step (l) thereby forming a phosphate triester,
wherein if R3 is selected from the first group a beta-amino function with R6=H is formed; and
wherein if R3 is selected from the second group an acylated beta-amino function is formed;

(m) capping the beta amino group of step (k) with acetanhydride in case that R3 consists of the first group of substituents, thereby introducing R6=acetyl, and proceeding with step (l), otherwise directly proceeding with step (m);

(n) reacting the compound of step (e) or the compound of step (d) with a further compound of Formula 3

(Formula 3)

wherein Acc, R1 and T1 are selected independently from each other and independently from Acc, R1 and T1 of the other monomer(s), thereby forming a protected and immobilized oligomer with a further monomer;

(o) capping free hydroxyl groups with acetanhydride or pivaloylanhydride;

(p) applying, if PG1 is a photo-cleavable protective group UV light to remove the protected and immobilized monomer, or an acid solution if PG1 is an acid-labile protective group to remove PG1 from the protected and immobilized monomer to from a new free hydroxyl group (q) repeating steps (i) to (p) z times, whereby z is an integer between 0 and 8;

(r) cleaving the permanent protective groups of the phosphoramidate moieties and the protective groups attached to R1 and R2 under basic conditions or under reducing conditions, if a cleavable linker was used in step (a) the linker is cleaved from the solid support to form a compound according to Formula 1;

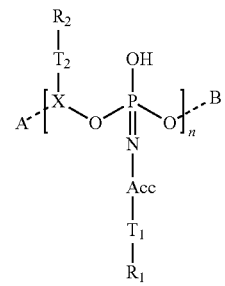
(Formula 1)

wherein B in Formula (1) is H,
if a non-cleavable linker was used in step (a) a compound according to Formula (1a) is formed;

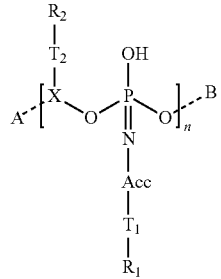
(Formula 1a)

wherein B in Formula (1a) is a non-cleavable linker; and
wherein A is selected from the group consisting of:
  a hydroxyl group,
  a phosphate, and
  a C3-C10 monoalkyl phosphate (—O—P═O(O)—O-alkyl), wherein said monoalkyl is linear, branched or a cycle and optionally substituted with a moiety selected from the group consisting of a detectable moiety and a reactive group selected from —SH, —NH$_2$, —O—NH$_2$, —NH—NH$_2$, —C(═O)H, —COOH, —CH═CH$_2$, —C═CH, and —OH;
in which B is selected independently from A and is selected from the group consisting of
  a hydrogen atom, and
  a C3-C10 alkyl, wherein said alkyl is linear, branched or a cycle, and optionally substituted with a moiety selected from the group consisting of a detectable moiety and reactive functional group selected from —SH, —NH$_2$, —O—NH$_2$, —NH—NH$_2$, —C(═O)H, —COOH, —CH═CH$_2$, —C═CH, —OH, and a solid support;
wherein n is an integer denoting the number of monomers, and n is equal to or greater than 2;
wherein each monomer Acc, R1, R2, T1, T2 and X are selected independently from each other and from the Acc, R1, R2, T1, T2 and X moieties of the other monomer(s);
wherein Acc is an electron acceptor selected from the group consisting of:
  a methyl-sulfonyl,
  a C6-C10 aryl-sulfonyl,
  a C5-C6 heteroaryl-sulfonyl with 1 or 2 heteroatoms selected from N, O, and S,
  a C5-C10 cycloalkyl-sulfonyl,
  a 6 membered electron-deficient aromatic ring, and
  a six-membered heterocycle with at least one alkylated N-atom in ortho- or para-position, said heterocycle being selected from the group consisting of pyridinium, pyrimidinium and chinolinium;
in which X is a spacer part consisting of 2-16 atoms, whereby the spacer part is selected from the group consisting of
  a branched or linear alkyl,
  a linear C4-C14 heteroalkyl with one N atom
  a branched or linear C4-C14 alkenyl,
  a branched or linear C4-C14 alkinyl,
  a bis-(C1-C3)-alkyl-(C6-C10)-aryl,
  a bis-(C1-C3)-alkyl-heteroaryl, with 5-6 membered heteroaryl with 1-3 heteroatoms selected from N, O and S
  a 5-10 membered cycloalkyl
  a 5-10 membered heteroalkyl structure with 2 heteroatoms, whereby each heteroatom is independently selected from N, O, and S, and
  a 5-10 membered cyclo-heteroalkyl structure with 1-5 heteroatoms, whereby each heteroatom is independently selected from N, O, and S;
in which the atom or atoms of X which are connected to phosphoramidate or A are sp$^3$ C atoms;
in which R1 is selected independently from R2, and R1 is directly or via a tether T1 attached to Acc;
wherein R2 is selected independently from R1, and R2 is directly or via a tether T2 to a C atom or (if present) N atom of X;
wherein R1 and R2 are selected from the group consisting of
  a hydrogen atom,
  a core moiety selected from the group consisting of
    a linear or branched C1-C6 alkyl group,
    a linear or branched C2-C6 alkenyl group,
    a linear or branched C2-C6 alkinyl group,
    a 5-10 membered cycloalkyl group,
    a 6-10 membered aryl group,
    a 5-10 membered heterocyclic group with 1-5 heteroatoms, whereby each heteroatom is independently selected from N, O, and S,
  a substituent attached to the core moiety, whereby the substituent is selected from the group consisting of
    a hydrogen atom,
    a halogen atom,
    a carboxyl group,
    a formyl group,
    a C1-C6 acyl group,
    a C6-C10 aroyl group,
    a hydroxyl group,
    a C1-C6 acylamino group,
    an amino group,
    a carboxamido group,
    a C1-C6 alkylmercapto group,
    a cyano group,
    a nitro group,
    a C1-C6 alkoxy group,
    a C1-C6 alkoxycarbonyl group,
    a C6-C10 aryloxy group,
    a C6-C10 aryloxycarbonyl group,
    a sulfhydryl group,
    a C6-C10 aryl- or C1-C6 alkyl-sulfonyl group,
    a phosphatyl group,
    a guanidyl group,
    a primary or secondary C1-C6 carboxamido group,
    a detectable moiety,
    a C6-C1 aryl group,
    a C2-C6 alkenyl group,
    a C2-C6 alkinyl group, and
    a 5-10 membered heteroaryl group,
  in which the tethers T1 and T2 are selected independently from each other, and a tether consists of a linear, branched or cyclic organic moiety comprising 1-30 C-atoms and 0-5 heteroatoms selected from N, O, and S, and 1-3 subunits selected from a carboxy moiety, an amide moiety and a urea moiety, whereby the internal heteroatoms with the exception of a disulfide bond are separated from each other by a minimum of two carbon atoms;
wherein for each monomer X, R1 and R2, and T1 and T2 are selected independently from the group consisting of X, R1 and R2, and T1 and T2 from other monomers, and
wherein the compound of Formula 1 or Formula 1a is a defined stereoisomer.

2. The method according to claim 1, wherein in a monomer R3 and R4 are —(CH$_2$)$_3$ and R5═H, and
wherein the stereo-genic carbon atom in the oxazaphospholidine is in either the R or S conformation, according to Formula 20 and Formula 21;

Formula 20

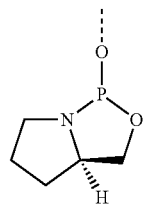

Formula 21

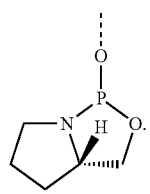

3. The method according to claim 1, wherein the carbon atom in a monomer X which is connected to T2 or R2 is a stereocenter.

4. The method according to claim 1, wherein in a monomer the P atom of the phosphoramidate moiety is a stereocenter.

5. The method according to claim 3, wherein for each monomer the stereoconformation of each stereocenter is selected independently from the respective stereocenters of the other monomers.

6. The method according to claim 1, wherein X does not contain a stereocenter.

7. The method according to claim 6, wherein X is a —(CH$_2$)$_3$— or a bis-p-methylenephenylene residue or a 3.5-bismethylenephenylene residue which is substituted with T2-R2 in the −1 position.

8. The method according to claim 3, wherein the monomer comprises a structure selected from the group consisting of Formulas (5) to (11):

Formula (5)

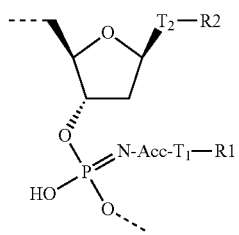

Formula (6)

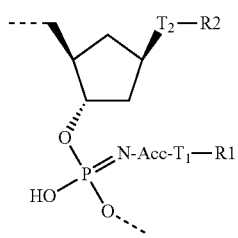

Formula (7)

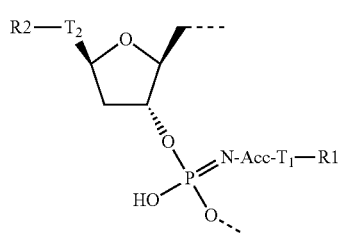

Formula (8)

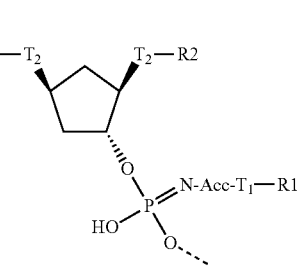

Formula (9)

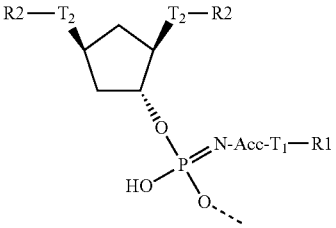

Formula (10)

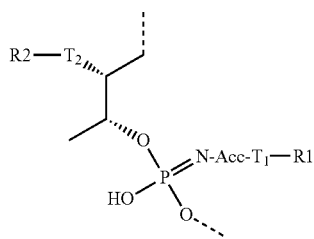

Formula (11)

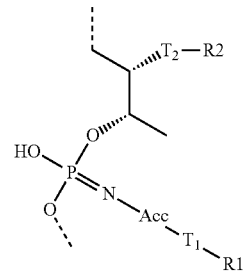

9. The method according to claim 8, wherein in a monomer T2 comprises a —C=O—NH— group or a —NH—C=O— group attached to the stereocenter of X.

10. The method according to claim 1, wherein n is between 2 and 10.

* * * * *

UNITED STATES PATENT AND TRADEMARK OFFICE
CERTIFICATE OF CORRECTION

PATENT NO. : 8,569,515 B2  Page 1 of 1
APPLICATION NO. : 13/099630
DATED : October 29, 2013
INVENTOR(S) : Dieter Heindl et al.

It is certified that error appears in the above-identified patent and that said Letters Patent is hereby corrected as shown below:

In the Claims

In Claim 1, Column 35, Line 37 should read as follows:

or if R3 is covalently linked to R4;

Signed and Sealed this
Tenth Day of December, 2013

Margaret A. Focarino
*Commissioner for Patents of the United States Patent and Trademark Office*